US011234666B2

(12) United States Patent
Chan et al.

(10) Patent No.: US 11,234,666 B2
(45) Date of Patent: Feb. 1, 2022

(54) APPARATUS AND METHOD FOR MEDICAL IMAGE RECONSTRUCTION USING DEEP LEARNING TO IMPROVE IMAGE QUALITY IN POSITION EMISSION TOMOGRAPHY (PET)

(71) Applicant: CANON MEDICAL SYSTEMS CORPORATION, Otawara (JP)

(72) Inventors: Chung Chan, Vernon Hills, IL (US); Jian Zhou, Vernon Hills, IL (US); Evren Asma, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 203 days.

(21) Appl. No.: 16/258,396

(22) Filed: Jan. 25, 2019

(65) Prior Publication Data
US 2019/0365341 A1 Dec. 5, 2019

Related U.S. Application Data

(60) Provisional application No. 62/704,008, filed on May 31, 2018.

(51) Int. Cl.
A61B 6/00 (2006.01)
A61B 6/03 (2006.01)
(Continued)

(52) U.S. Cl.
CPC ............ *A61B 6/5258* (2013.01); *A61B 6/032* (2013.01); *A61B 6/037* (2013.01); *G06N 3/08* (2013.01);
(Continued)

(58) Field of Classification Search
CPC ................... G06T 7/0012; G06T 5/002; G06T 2207/20084; G06T 2207/10004;
(Continued)

(56) References Cited

U.S. PATENT DOCUMENTS 10,078,889 B2    9/2018  Zhu et al.
2015/0289825 A1* 10/2015 Lage ..................... G06T 11/005
                                                    600/425
2016/0116603 A1  4/2016  Chen et al.

FOREIGN PATENT DOCUMENTS

WO    WO 2017/191643 A1    11/2017

OTHER PUBLICATIONS

Xu J, Gong E, Pauly J, Zaharchuk G. 200x low-dose PET reconstruction using deep learning. arXiv preprint arXiv:1712.04119. Dec. 12, 2017, (Year: 2017).*

(Continued)

*Primary Examiner* — Vu Le
*Assistant Examiner* — Tracy Mangialaschi
(74) *Attorney, Agent, or Firm* — Oblon, McClelland, Maier & Neustadt, L.L.P.

(57) ABSTRACT

A deep learning (DL) convolution neural network (CNN) reduces noise in positron emission tomography (PET) images, and is trained using a range of noise levels for the low-quality images having high noise in the training dataset to produceuniform high-quality images having low noise, independently of the noise level of the input image. The DL-CNN network can be implemented by slicing a three-dimensional (3D) PET image into 2D slices along transaxial, coronal, and sagittal planes, using three separate 2D CNN networks for each respective plane, and averaging the outputs from these three separate 2D CNN networks. Feature-oriented training can be implemented by segmenting each training image into lesion and background regions, and, in the loss function, applying greater weights to voxels in the lesion region. Other medical images (e.g. MRI and CT) can be used to enhance resolution of the PET images and provide partial volume corrections.

11 Claims, 17 Drawing Sheets

(51) Int. Cl.
*G06N 3/08* (2006.01)
*G06T 7/00* (2017.01)

(52) U.S. Cl.
CPC .. *G06T 7/0012* (2013.01); *G06T 2207/10004* (2013.01); *G06T 2207/20081* (2013.01); *G06T 2207/20084* (2013.01)

(58) Field of Classification Search
CPC . G06T 2207/10104; G06T 2207/20081; A61B 6/037; A61B 6/032; A61B 6/5258; G06N 3/08
See application file for complete search history.

(56) References Cited

OTHER PUBLICATIONS

Matviychuk, Yevgen, et al. "Learning a multiscale patch-based representation for image denoising in X-ray fluoroscopy." 2016 IEEE International Conference on Image Processing (ICIP). IEEE, 2016. (Year: 2016).*
Xiang, Lei, et al. "Deep auto-context convolutional neural networks for standard-dose PET image estimation from low-dose PET/MRI." Neurocomputing 267 (2017): 406-416. (Year: 2017).*
The partial European Report dated Oct. 18, 2019 in European Patent Application No. 19177508.9, 14 pages.
Shan, H. et al."3D Convolutional Encoder-Decoder Network for Low-Dose CT via Transfer Learning from a 2D Trained Network", IEEE Transactions on Medical Imaging, XP081434403, 2018, 12 pages.
Khullar, S. et al. "Wavelet-based fMRI analysis: 3-D denoising, signal separation, and validation metrics", NeuroImage. vol. 54, No. 4, XP027589531, 2011, pp. 2867-2884.
Gong, K. et al. "PET Image Denoising Using Neural Network", IEEE Nuclear Science Symposium and Medical Imaging Conference (NSS/MIC), IEEE, XP033446049, 2017, 2 pages.
A. Bevilacqua, et al., "A New Approach to Image Reconstruction in Positron Emission Tomography Using Artificial Neutral Networks", International Journal of Modern Physics C, vol. 9, No. 1, 1998, pp. 71-85.
S. Ahn, et al., 'Quantitative comparison of OSEM and penalized likelihood image reconstruction using relative difference penalties for clinical PET', Phy. Med. Biol., 2015.
G. Wang and J. Qi, 'Penalized likelihood PET image reconstruction using patch-based edge-preserving regularization', IEEE Trans. Med. Imag., 2012.
C. Chan, et al., 'Postreconstruction nonlocal means filtering of whole-body PET with an anatomical Prior', IEEE Trans. Med. Imag., 2014.
C. Chan, et al., 'Regularized image reconstruction with an anatomically adaptive prior for positron emission tomography', Phy. Med. Biol., 2009.
L. Cheng, et al., 'Accelerated iterative image reconstruction using a deep learning based leapfrogging strategy', Proceeding of Fully3D, 2017.
L. Xiang, et al., 'Deep auto-context convolutional neural networks for standard-dose PET image estimation from low-dose PET/MRI', Neurocomputing, 2017.
K. Gong, et al., 'Iterative PET image reconstruction using convolutional neural network representation', arxiv, 2017.
J. Xu, et al., '200x Low-dose PET Reconstruction using Deep Learning', PET/MR workshop, 2017.
Extended European Search Report dated Jan. 31, 2020 in Patent Application No. 19177508.9, 15 pages.
Martin Sewell, "Ensemble Learning" Tech. Rep. RN/11/02, Retrieved from the Internet: URL:https://web.archive.org/web/20170525020355/ http://machine-learning.martinsewell.com/ensembles/, XP055659581, Aug. 1, 2008, pp. 1-16.
Office Action dated Oct. 28, 2021 in European Application No. 19177508.9.

\* cited by examiner

APPARATUS AND METHOD FOR MEDICAL IMAGE RECONSTRUCTION USING DEEP LEARNING TO IMPROVE IMAGE QUALITY IN POSITION EMISSION TOMOGRAPHY (PET)

CROSS-REFERENCE TO RELATED APPLICATIONS

This application is based upon and claims the benefit of priority to provisional U.S. Application No. 62/704,008, filed May 31, 2018, the entire contents of which are incorporated herein by reference.

FIELD

This disclosure relates to using deep learning (DL) networks to improve the image quality of reconstructed positron emission tomography (PET) images, and, more particularly, to (i) training a DL network to be robust to variations in a noise level of the input PET image, (ii) implementing the DL network using multiple two-dimensional (2D) convolution neural networks applied in parallel to respective 2D slices in the sagittal, coronal, and transaxial planes, (iii) training DL network to preserve small/fine features by using a feature oriented training strategy to weight, in the loss function, voxels corresponding to lesion and/or regions of interest, and/or (iv) use other medical images to enhance resolution and correct for partial volumes effects (PVE).

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

In PET imaging, a tracer agent is introduced into the patient, and the physical and bio-molecular properties of the agent cause it to concentrate at specific locations in the patient's body. The tracer emits positrons, resulting in an annihilation event occurs when the positron collides with an electron that produces two gamma rays (at 511 keV) traveling at substantially 180 degrees apart.

PET imaging systems use detectors positioned around the patient to detect coincidence pairs of gamma rays. A ring of detectors can be used in order to detect gamma rays coming from each angle. Thus, a PET scanner can be substantially cylindrical to maximize the capture of the isotropic radiation of gamma rays. A PET scanner can be composed of several thousand individual crystals (e.g., Lutetium Orthosilicate (LYSO) or other scintillating crystal) that are arranged in two-dimensional scintillator arrays and packaged in modules with photodetectors to measure the light pulses from respective scintillation events. For example, the light from respective elements of a scintillator crystal array can be shared among multiple photomultiplier tubes (PMTs), or can be detected by silicon photomultipliers (SiPMs) having a one-to-one correspondence with the elements of the scintillator crystal array.

To reconstruct the spatio-temporal distribution of the tracer via tomographic reconstruction principles, each detected event can be characterized for its energy (i.e., amount of light generated), its location, and its timing. By detecting the two coincident gamma rays, and drawing a line between their locations, the line-of-response (LOR) can be determined, corresponding to the likely location of the original disintegration. Using the timing information, a time-of-flight (TOF) analysis can be used to narrow the likely location of the original disintegration to a statistical distribution (e.g., a Gaussian curve) along the LOR. While this process will only identify a line/region for the location of the original disintegration, by accumulating a large number of coincidence counts, a tomographic reconstruction process can estimate an image of the activity distribution (e.g., the tracer density within the patient).

As discussed above, the LOR for coincidence pairs and the timing information is used to reconstruct a tomographic image of the radioactivity, yielding clinical information. However, this clinical information can often be obscured by noise and/or scatter. Noise can be mitigated to a degree using various denoising methods, but some denoising methods can introduce artifacts into the image and produce non-uniform image quality depending on the noise level of the input image.

Even for relatively long PET scan/acquisition times, the practical limitations associated with injection dose of tracer and scan durations cause PET images to typically suffer from high noise levels and relatively poor spatial resolution. Consequently, the low-image quality typically of PET images can lead to misdiagnoses and incorrect treatment decisions, especially when the noise level varies significantly among the reconstructed PET images. The variability in the noise level can be further compound when denoising methods applied to the reconstructed PET images are susceptible to noise-level dependent artifacts.

Thus, better denoising methods are desired for PET imaging, especially denoising methods that are robust to variations in the noise level of the reconstructed PET images.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
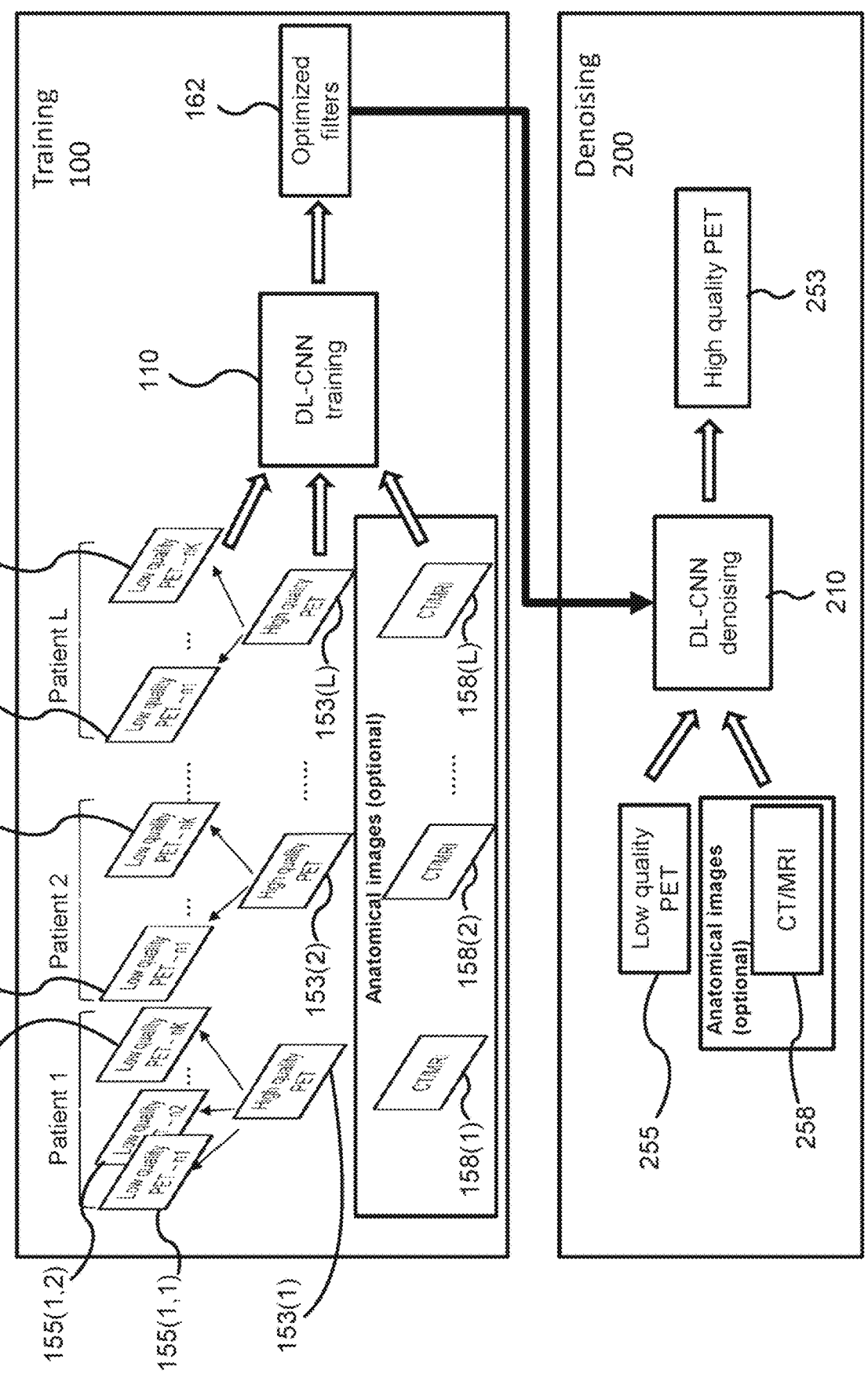
FIG. 1 shows a flow diagram of an example of a method 100 that trains a deep-learning (DL) convolutional neural network (CNN) and then, in another method 200, applies low-quality PET images to the DL-CNN network to reduce the noise, according to one implementation.

Several challenges can thwart efforts to consistently obtain high-quality images from positron emission tomography (PET) imaging. For example, due to limitations in injected doses and scan durations, the image quality of PET images often suffers due to high noise and poor spatial resolution (e.g., 5-7 mm). These effects can lead to misdiagnoses and incorrect treatment decisions.

Additionally, the high noise levels and poor spatial resolution can hamper both the detectability of small and/or low contrast lesions and the quantitative accuracy of PET. The image quality can often be further degraded by other confounding factors, such as positron range, photon pair non-collinearity, limited intrinsic system resolution, finite reconstruction voxel sizes, patient motion etc. In addition, numerous acquisition-related factors can affect PET image quality such as variability in the scan protocol, patient body mass and physiology, injection dose, time between injection and start of the scan, etc. Thus, the intra- and inter-patient image quality can vary significantly. The large variability of image quality can make treatment assessment challenging because this variability makes it difficult to compare scans acquired at different times and/or for different patients.

To address the above-identified challenges, the methods described herein apply methods in deep learning (DL) and convolutional neural networks (CNN) to obtain consistently high-quality images from PET data with a large degree of variability (e.g., different noise levels). The DL-CNN network described herein can produce output images having a uniform image quality, even when the input images exhibit large variations in their image quality and statistical properties (e.g., by having different noise levels).

Related noise suppression methods suffer from various deficiencies that are remedied or mitigated by the methods described herein. For example, image quality can be improved through either regularization approaches or post-reconstruction filtering approaches.

In a regularization approach, a user defined penalty function is incorporated into an objective/cost function that is optimized to iteratively reconstruct an image of the activity level (e.g., tracer density) within the respective voxels (i.e., volume pixels) of the reconstructed image. The user defined penalty function can, e.g., encourage local smoothness and thus supress noise. Some regularizer can be tailored/optimized with the goal of differentiating noise and lesions (e.g., suppressing noise without reducing the signal derived from lesions or other features of interest). That is, the background noise is suppressed while lesions are preserved.

In a post-reconstruction filtering approach, a linear Gaussian filter or a non-linear filter such as a non-local means filter or median filter can be applied to suppress noise, thereby improving the signal to noise ratio (SNR). This noise suppression, however, is typically accompanied by an undesired reduction in resolution (e.g., fine details and sharp boundaries can be blurred and detail lost).

Compared to regularized reconstruction and post-reconstruction filtering processes, the DL-CNN approaches described herein provide several advantages. First, the DL-CNN approaches described herein can provide better clinical confidence by yielding more consistent noise texture (making comparisons between PET images simpler and more straightforward). Second, the DL-CNN approaches described herein can provide improved robustness and repeatability in a clinical setting because they do not require parameter selection or adjustments to be optimized by the user.

Additionally, the methods described herein offer several advantages compared to related DL-CNN approaches. For example, in some related DL-CNN approaches, the CNN is trained to allow more rapid convergence to the reconstructed image without improving the image quality of the reconstructed image.

In a second related DL-CNN approach, the CNN is trained with poor-quality images having a uniform level of noise. Thus, the CNN is optimized to be effective for filtering images that have the same level of noise as the training images, but can produce poor results when filtering an images that diverges from noise level of the training data. Further, these CNNs can be susceptible to loss of low-contrast details because the large contribution to the error function from the large number of voxels in the background, which benefit predominantly from smoothing, can overwhelm the small contribution to the error function arising from the few number of voxels in a region of interest (e.g., the region of a lesion) that exhibits fine detail and requires higher resolution. This is because the second related DL-CNN approach lacks a mechanism to rebalance the loss function used to train the CNN in order to more heavily weight/emphasize the signals in a region of interest relatively the larger background regions, in order to train the network to preserve small features and fine details in the images.

In a third related CNN approach, the CNN is used as a prior in the reconstruction process, rather than as a filter applied post-reconstruction. In this approach, the cost function is difficult to optimize, and the optimization approach does not guarantee convergence. Additionally, parameter selection remains a challenge (as in the above-mentioned regularization based approaches), making this approach less reliable and less robust.

In contrast to the related DL-CNN approaches discussed above, the DL-CNN approach described herein makes the network more robust to variations in the noise levels of the input PET images. As discussed above, these variations in the noise levels can occur due to variance in acquisition and reconstruction protocols. Further, the methods described herein provide more consistent results with consistent image quality, when the noise level of the input PET image is with a range of noise levels used in training the DL-CNN network. This uniformity and consistent in the image quality of the output PET images can lead to reduced inter- and intra-patient variation in the images, and better diagnostic and clinical outcomes. The methods described herein also provide fewer or less-severe artifacts in coronal or sagittal views, due to the use of a computationally-efficient 2.5D orthogonal training and denoising approach. Finally, the methods described herein provide better preservation of small-lesion contrast and improved image resolution, which is achieved by using feature-oriented training approach and by using anatomical information and other types medical images (e.g., magnetic resonance imaging (MRI) and X-ray computed tomography (CT)) in training and applying the DL-CNN network.

The above-identified improvements are variously achieved by the features of the methods described below. For example, the methods described herein apply a DL-CNN approach to improve PET image quality by suppressing noise while preserving lesions. This approach is tailored to automatically adapt to different noise levels in the input images while producing similar quality output images, without the need to tweak the denoising method through adjustable parameters in order to adapt the denoising method to variations in the input image (e.g., fine-tuning that either has to be performed by a user or requires a statistical analysis of the input image). Rather, after the DL-CNN network has been trained according the methods described herein, the trained DL-CNN can be used with input images spanning a wide range of statistical properties (e.g., noise levels) without changes or adjustable parameters, thereby reducing intra- and inter-patient image-quality variations.

The above improvements are variously realized by the features of (i) the CNN being trained such that the image denoising performed by the CNN is largely independent of the noise levels of the input image, (ii) the CNN architecture applying a 2.5D orthogonal training and denoising approach (as opposed to a purely 2D or 3D approach), (iii) a feature-oriented training approach focused on preserving small and low-contrast signals, and (iv) the CNN being trained using a multi-modality training and denoising for partial volume correction.

Figure 2:
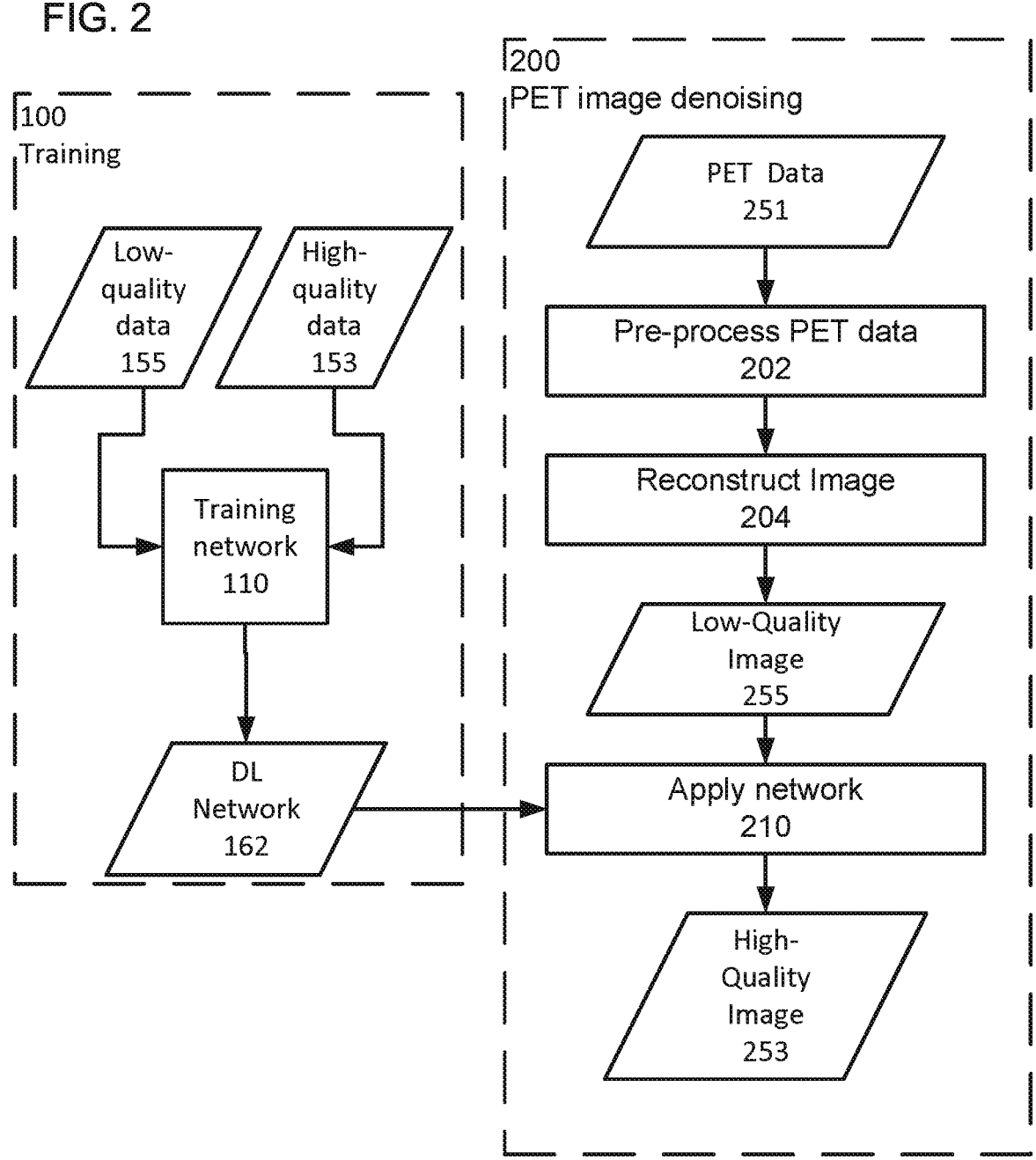
FIG. 2 shows another flow diagram of methods 100 and 200 being applied to denoise the PET images, according to one implementation.

Referring now to the drawings, wherein like reference numerals designate identical or corresponding parts throughout the several views, FIG. 1 shows a flow diagram of method 100 for training a DL-CNN network 162 and method 200 for applying a low-quality (e.g., noisy) PET image 255 to the trained network 162 to generate a high-quality (e.g., denoised) PET image 235. Another flow diagram illustrating method 100 and method 200 is shown in FIG. 2, according to another implementation.

In method 100, a loss function is used to iteratively adjust parameters (e.g., weights and biases of convolutional and pooling layers) of DL-CNN network until stopping criteria are satisfied (e.g., convergence of the parameters to a predefined threshold) to generate the trained network 162. The loss function compares high-quality data 153 to results of a current version of the DL-CNN network to which low-quality data 155 is applied. In the case of PET imaging, the high- and low-quality data are reconstructed PET images with high/good image quality and low/poor image quality, respectively. As shown in FIG. 1, the network 162 is made to be robust to varying levels of noise by being trained using various samples of low-quality data having different levels of noise. In general, the signal-to-noise ratio (SNR) is smaller when the image is reconstructed using a smaller dataset (e.g., due to a shorter scan time or other factors resulting in fewer coincidence counts). Accordingly, the high-quality image 153(1) can be generated using all of the coincidence counts from a PET scan of a first patient (i.e., patient 1) to generate a PET image the highest possible image quality. Then the lower quality images 155(1,1), 155(1,2), . . . ,155(1,k) reconstructed from the scan of patient 1 can be generated using various subsets of coincidence counts selected from the full dataset, each of these lower quality images corresponding to a different number of counts and therefore resulting in reconstructed images having a range of noise levels. Similarly, different noise levels can be obtained for the low-quality images 155(2,1), 155(2,2), . . . ,155(2,k) from subset of a full dataset generated from a PET scan of patient 2, and all other patients up to a last patient (i.e., patient L for whom the low-quality images are 155(L,1), 155(L,2), . . . ,155(L,k) and the high-quality image is 153(L)).

Optionally, the training method 100 can also incorporate other medical images 158 that are generated from medical imaging scan performed using another medical imaging modality (e.g., X-ray computed tomography (CT) or magnetic resonance imaging (MIR)). The other medical imaging scan performed can be performed in concert/simultaneously with the PET scan or in close temporal proximity to the PET scan. The other medical scan can advantageously be used to provide an attenuation model and provide enhanced resolution.

For example, in a PET/MRI scanner, the other medical images 158 can be MRI images. In FIG. 1, the MRI image 158(1) is acquired for patient 1 and corresponds to the high-quality PET image 153(1). Similarly, the MRI image 158(2) is acquired for patient 2 and corresponds to the high-quality PET image 153(2), and the MRI image 158(L) is acquired for patient L and corresponds to the high-quality PET image 153(L).

In another example for a PET/CT scanner, the other medical images 158 can be computed tomography (CT) images.

After generating the trained network 162, method 200 is used to apply the trained network 162 to generate a high-quality PET image 253, independently of the noise level in the low-quality PET image 255 reconstructed from the PET emission data 251. That is, the approach in step 110 in which the network 162 is trained using low-quality images having a wide range of noise levels can reduce the dependence of the image quality of the high-quality PET image 253 on the noise level of the low-quality PET image 255, relative to other training approaches in which the low quality images all have similar noise levels.

In certain implementations, the PET data 251 can be counts that are pre-processed at step 202 (e.g., signal pre-conditioning, position corrections, energy corrections, etc.), and then, at step 204, the pre-processed count data is used to reconstruct an image of radioactivity level (e.g., tracer density) as a function of voxel position.

In method 200, the PET emission data 251 is corrected in step 202, and then, in step 204, a PET image 255 is reconstructed from the corrected emission data using a PET image reconstruction process.

In step 202, the emission data can be corrected using various calibration and geometric factors. For example, the pre-processing can include corrections for a detector offset and gain, variations in quantum efficiency in the detectors, etc. Further, these corrections can be based on calibration data, empirical, and known parameters.

In step 204, the image reconstruction can be performed using a back-projection method, a filtered back-projection method, a Fourier-transform-based image reconstruction method, an iterative image reconstruction method, a matrix-inversion image reconstruction method, a statistical image reconstruction method, a list-mode method, or other reconstruction method as would be understood as a person of ordinary skill in the art.

In step 210, the reconstructed image is denoised using the DL-CNN network 162. The result of which is a high-quality image 253. Thus, noisy PET images resulting from the PET reconstruction in step 204 can be processed using a DL denoising algorithm applying the network generated by the offline DL training method 100. Because the network 162 has been trained using low-quality images 155 of varying noise levels, the high-quality image 253 should be produced with a uniformly high image quality, independently of the noise level in the reconstructed image from step 204. That is, the PET image noise for in the reconstructed image from step 204 can be influenced by many factors such as injected dose, patient size, patient physiology, wait time from injection to the start of the scan, reconstruction parameters, etc. In fact, any one of these factors can by itself be sufficient to affect the noise level in the resulting PET image. Moreover, the noise distribution can also vary spatially within a given PET image. Nevertheless, due to the training approach in step 110, the high-quality image 253 can be produced with uniform high quality, making possible improved clinical comparisons among the PET images generated that are using the combination of methods 100 and 200 disclosed herein.

In contrast to related methods that require an initially statistical analysis of the low-quality image 255 to pre-determine the noise level in the input images and then adjust the reconstruction method to compensate for the pre-determined noise level, a better approach, which is applied in the methods described herein, is to train the DL-CNN network 162 using reconstructed images have a variety of noise levels, making the DL-CNN network robust to variations in the noise level of the input image. Otherwise, a DL-CNN network trained with low-quality images of a fixed level might lead to inferior denoising results or artifacts when applied to images with mismatched noise levels.

In certain implementations, the multi-noise level training of the network 162 is carried out as described below in order to achieve noise-adaptive denoising (i.e. consistent denoising results across a range of noise levels and statistical properties of the reconstructed images arising from variations in patients and PET scans/protocols). For each of the full PET list-mode training datasets (e.g., a respective full PET list-mode training dataset corresponds to each of the L patients shown in FIG. 1), the full dataset is rebinned into smaller subsets of the full dataset, each subset having a predefined percentage/amount of the full dataset. This rebinning creates a variety of sizes for the training datasets used to reconstruct for the low-quality PET images that are used to train the network 162. For example, each of the full PET list-mode training datasets can be rebinned into a wide range of count levels (e.g., noise level 1, 2, . . . K as shown in FIG. 1, corresponding to 10%, 20%, . . . , 90% of the full dataset). This rebinning can be achieved, e.g., by uniformly/randomly sampling the full list-mode dataset to create a subset.

Next, each of these subsets can then be used to reconstruct a PET image. In certain implementations, this reconstruction can be standardized by using the same reconstruction method and parameters to reconstruct the respective low-quality images corresponding to different noise levels (i.e., the different noise levels arises from the differences in the sizes of the subsets from which they are reconstructed—not from variations in the reconstruction process). In certain implementations, the high-quality image can be reconstructed using the full list-mode dataset and using the standardized reconstruction methods and parameters that are used for reconstructing the low-quality images. In such a case, the discrepancies between the high-quality image and the low-quality images for a given scan/patient can mainly be attributed to noise resulting from the reduced size of the subsets.

After obtaining the training data, as described above, the DL-CNN network is trained by adjusting various optimizing parameters to minimize a loss function calculated between training pairs for each scan/patient, which each include the high-quality image for the scan/patient and a corresponding low-quality image (i.e., for patient 1 the pairs can be $\{153(1), 155(1,1)\}, \{153(1), 155(1,2)\}, \ldots, \{153(1), 155(1,k)\}$). Because the network 162 is trained to using a wide range of noise levels for the low-quality images, the trained network 162 can be expected to generate consistently high-quality PET images regardless to the noise level in the input image without the need of adjustable parameters when the trained network 162 is used in step 210. That is, all of the adjustments and tuning are performed in step 110, such that in step 210 the trained network 162 can be used without an additional adjustments or tweaking tailored to the noise level of the input image 255.

Now a non-limiting first example of an implementation of methods 100 and 200 is provided. In this first example, a deep residual learning framework is applied for image denoising. Let x be the clean image, and y be the noisy observation corrupted by additive noise n (i.e., y=x+n). The goals of the deep residual network is to estimate the noise n from the input noisy image y (i.e., $\mathcal{F}(y)\approx n$), wherein $\mathcal{F}$ is the residual mapping process. The denoised image $\hat{x}$ can then be obtained by subtracting the estimated noise $\mathcal{F}(y)$ from the reconstructed image y (i.e., $\hat{x}\approx y-\mathcal{F}(y)$). In certain implementations, the loss function can be formulated as $$L(\Theta) = \frac{1}{N}\sum_{i\in N}\psi(F(y_i;\Theta)-(y_i-x_i)),$$

wherein Θ denotes the trainable weights, ψ is the error function (e.g., a mean square error (MSE) is used in the first example), N represents the number of training samples, y denotes the noisy images, and x denotes the target images. In the first example, stochastic gradient descent is used to minimize the loss function, and an eight layers network is used, providing a good balance between performance and training efficiency. The network architecture is shown in Table 1. In Table 1, "Cony" denotes a convolution layer, "BN" denotes batch normalization, and "ReLU" denotes the rectified linear unit. In the first example, the training dataset eight scans lasting fourteen minutes each. These full datasets were used to generate the high-quality images, and uniform rebinning of these full datasets was used to generate subsets corresponding to 60, 120, 180, 240, 300, and 420 second long scans, which were used to generate the low-quality images. These training datasets were then used to train the network, with the images being reconstructed using an ordered-subset expectation maximization method (OS-EM).

Figure 3A:
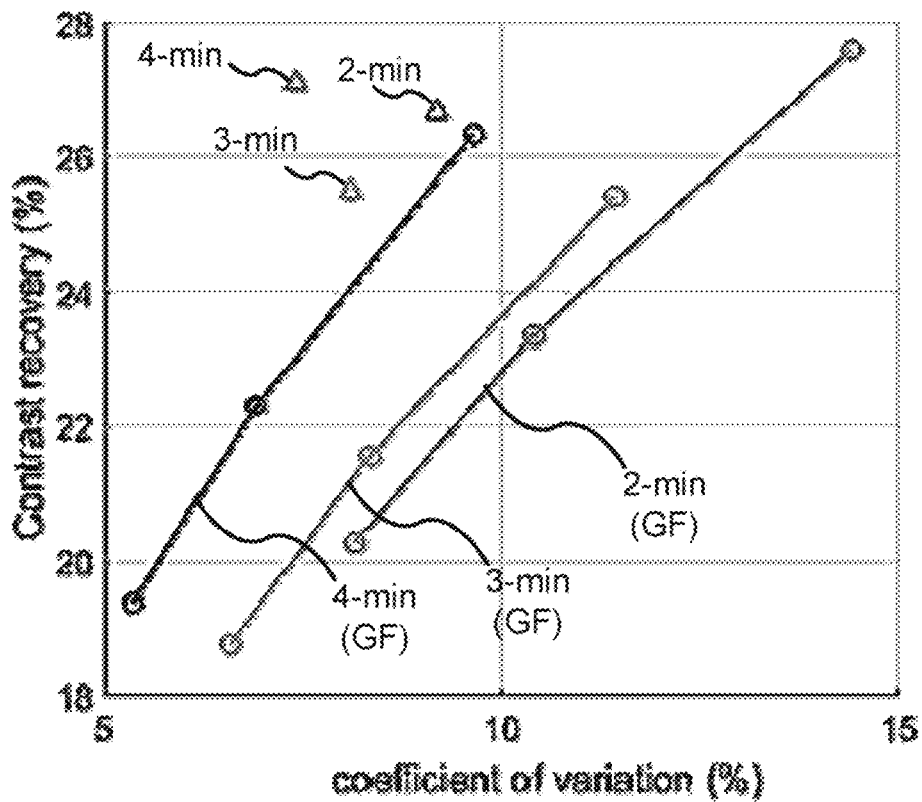
FIG. 3A shows a plot of the contrast recovery (vertical axis) versus the liver coefficient of variation (horizontal axis) for a lung region in a PET image that has been denoised (i) using a DL-CNN network, according to one implementation and (ii) using a Gaussian filter, the PET images corresponding to acquisition times of 2, 3, and 4 minutes.
Figure 3B:
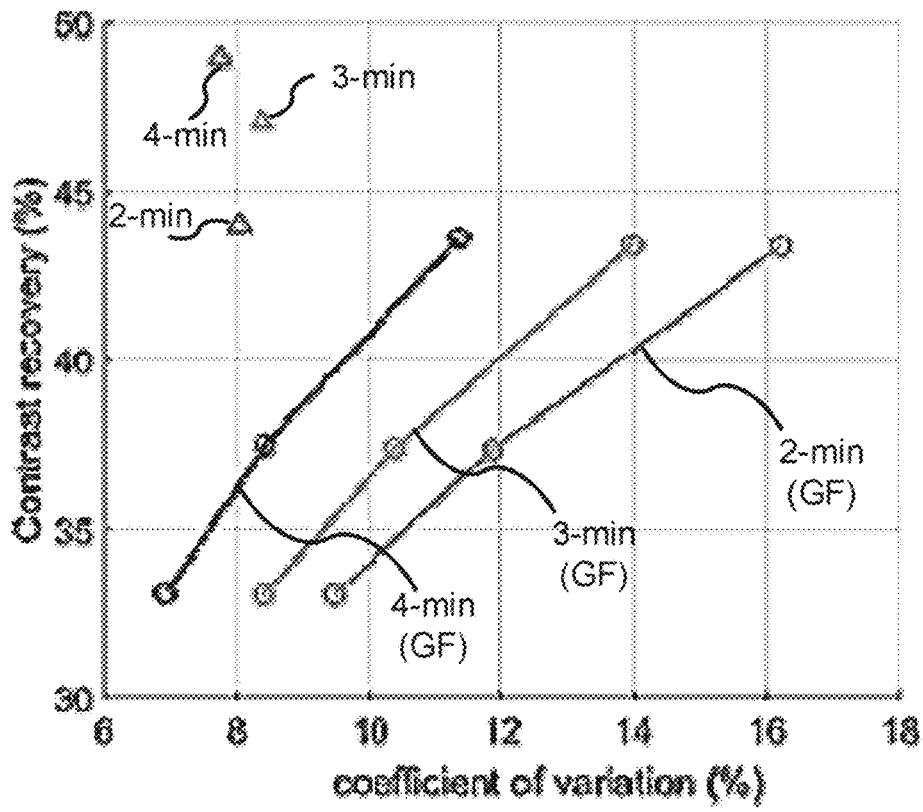
FIG. 3B shows a plot of the contrast recovery (vertical axis) versus liver coefficient of variation (horizontal axis) for a liver region in the PET image that has been denoised (i) using a DL-CNN network, according to one implementation and (ii) using a Gaussian filter, the PET images corresponding to acquisition times of 2, 3, and 4 minutes.

To test/validate the DL-CNN network 162, the DL-CNN network 162 was then applied to OS-EM reconstructed images obtained for 2, 3, and 4 minute long PET scans, and the results compared to denoising using Gaussian filters having respective widths of 4, 6, and 8 mm at full-width half maximum (FWHM). FIGS. 3A and 3B show graphs of the "contrast of recovery" plotted versus the "coefficient of variation" for two different regions within the OS-EM reconstructed images for the 2, 3, and 4 minute long PET scans after denoising (FIG. 3A is for a lung region and FIG. 3B is for a liver region). The images that are denoised using the DL-CNN network 162 (shown using the triangle symbol) tend to be more tightly grouped than images that have been denoised using a Gaussian filter (GF), which are shows using a circle symbol, thus confirming that the DL-CNN network-based method tends to be robust to variations in the noise level of the reconstructed image. Additionally, the images that have been denoised using the DL-CNN network-based method tend to have better image quality than those denoised using a Gaussian filter.

TABLE 1

Architecture of the deep residual network for the first example.

| layer | Layer Functions | | |
|---|---|---|---|
| 1 | Conv | ReLU | |
| 2 | Conv | BN | ReLU |
| 3 | Conv | BN | ReLU |
| 4 | Conv | BN | ReLU |
| 5 | Conv | BN | ReLU |
| 6 | Conv | BN | ReLU |
| 7 | Conv | BN | ReLU |
| 8 | Conv | | |

Figure 4:
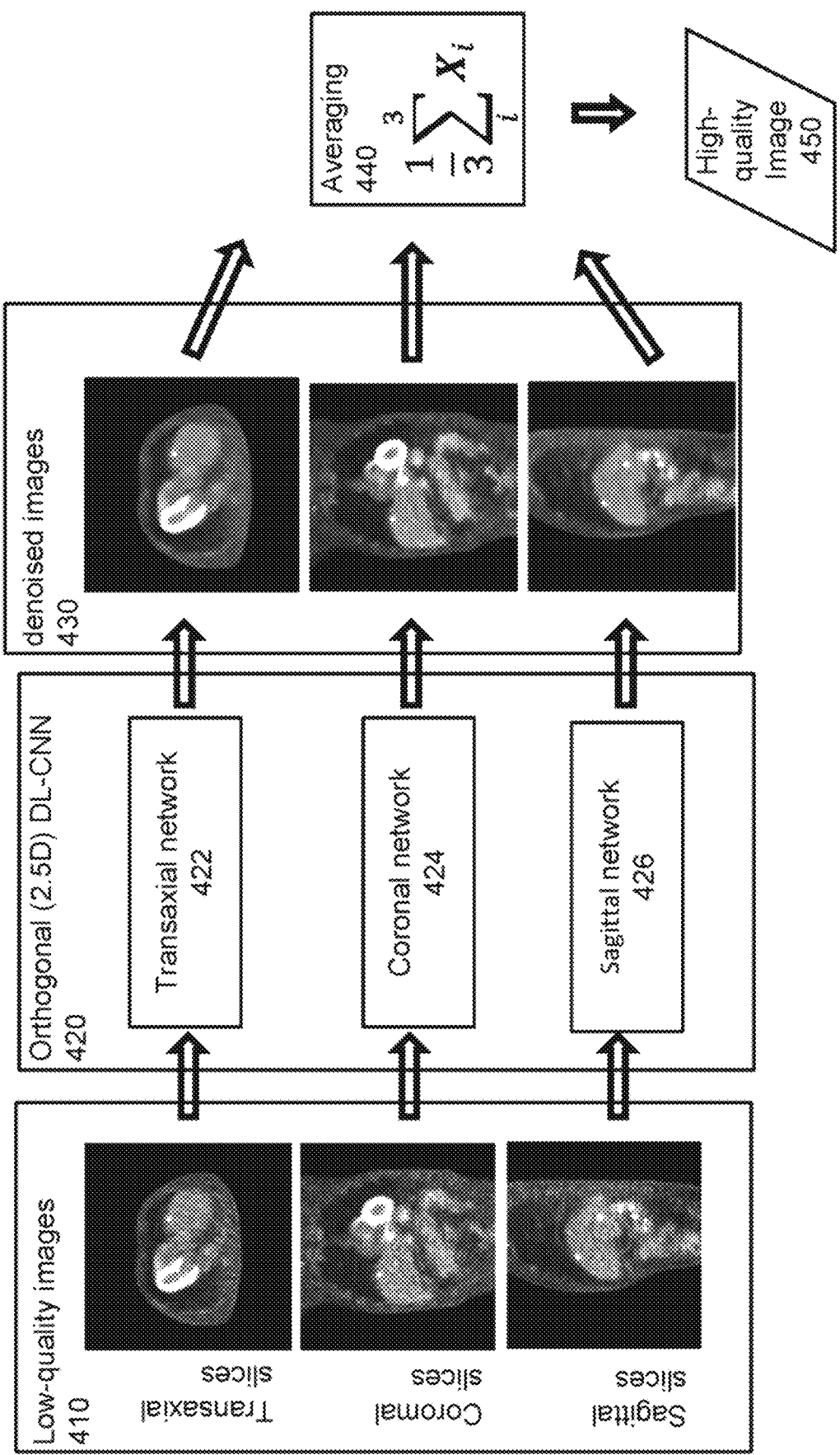
FIG. 4 shows a flow diagram of a process 400 for applying a 2.5-dimensional (2.5D) DL-CNN network to a three dimensional (3D) PET image, according to one implementation.

FIG. 4 shows a 2.5D process 400 that can be used when performing the DL-CNN network-based filtering/denoising (i.e., in steps 110 and 210). In process 400, the DL-CNN network 162 can include three networks that are respectively applied to two-dimensional (2D) slices of the reconstructed three-dimensional (3D) PET image, each of the three networks corresponding to a different orientation. That is, the transaxial network 422 can be applied to 2D slices that are parallel to a transaxial plane of the 3D PET image. Similarly, the coronal network 424 can be applied to 2D slices that are parallel to a coronal plane of the 3D PET image, and the sagittal network 426 can be applied to 2D slices that are parallel to a sagittal plane of the 3D PET image.

In step 410 of process 400, the low-quality PET image is sliced according to the respective planes/orientations.

In step 420 of process 400, the respective DL-CNN networks 422, 424, and 426 are applied to slices in their respective planes to generate the denoised images 430.

In step 440 of process 400, the denoised images are combined to form an aggregate image. For example, the three denoised images 430 can be averaged, resulting in a single 3D denoised image.

This 2.5D approach offers several advantages over both 2D and 3D approaches to denoising a low-quality PET image. In contrast to the 2.5D approach, a 3D approach can be computationally slow and burdensome. Further, a purely 2D approach, which operates only on 2D slices parallel to a single plane can fail to mitigate artifacts and utilize spatial information parallel to the other planes.

Whereas PET imaging provides 3D volumetric information of the radiotracer uptake inside the body, other DL-CNN approaches operate on 2D images, which may yield streak artifacts on 3D volumetric datasets. For example, when DL-CNN operates on transaxial views, it ignores voxel-wise correlations in the coronal and sagittal directions leading to streak artifacts in coronal and sagittal views. While these artifacts could be addressed by adopting a CNN network using fully 3D convolutions, such a fully 3D convolution in DL-CNN is computationally expensive for both training and denoising.

Thus, process 400 uses a 2.5D solution that still uses 2D convolutions in the DL-CNN network 162, but in the 2.5D solution the 2D slices are not limited to being parallel to a single plane.

In certain implementations, process 400 trains three orthogonal networks using the training samples sliced in each of the orthogonal views (e.g., transaxial, coronal and sagittal). Each orientation of slice data can be processed by the corresponding network. These three denoised 3-D volumes are then combined (e.g., averaged) to obtain the final result—the high-quality image 253. When process 400 is used, it is used in both step 110 to train the data and in step 210 to denoise the data.

Figure 5:
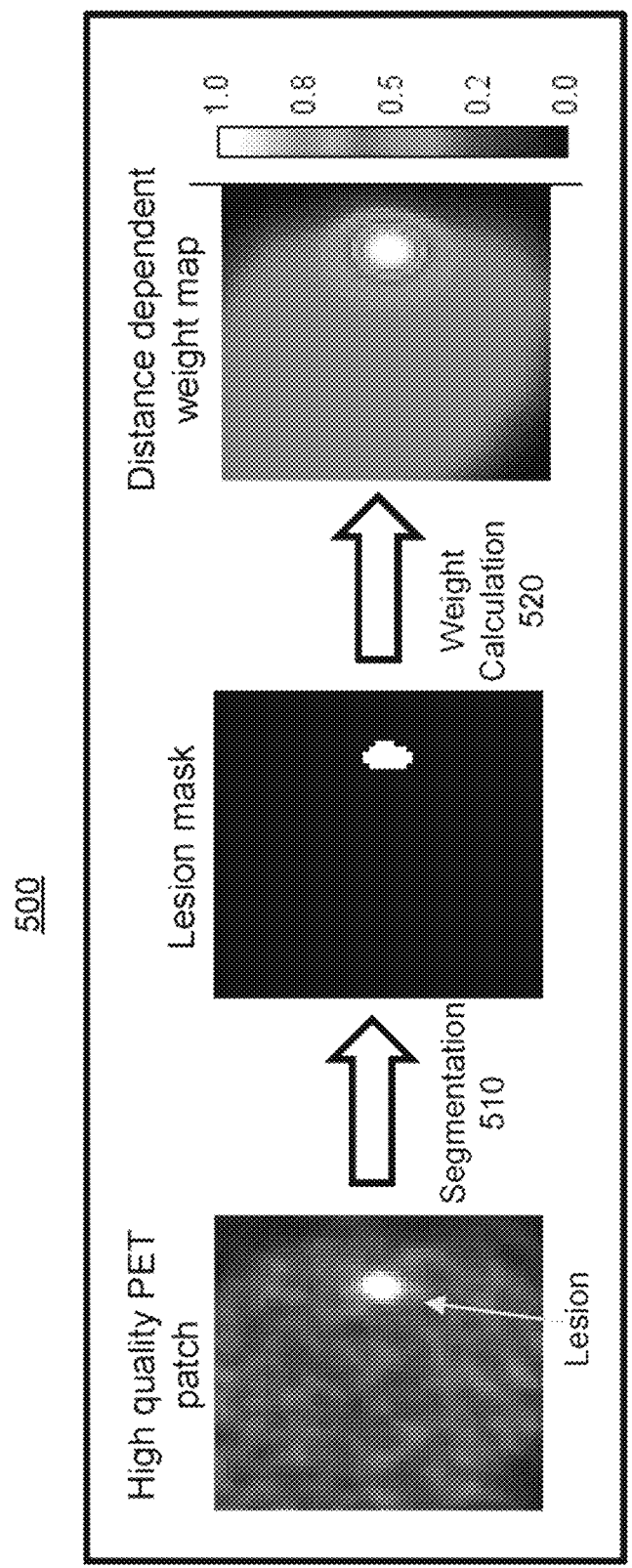
FIG. 5 shows a flow diagram of a process 500 for determining weight maps that are applied in step 110', which is step 110 that has been modified to use feature-oriented training, according to one implementation.
Figure 6:
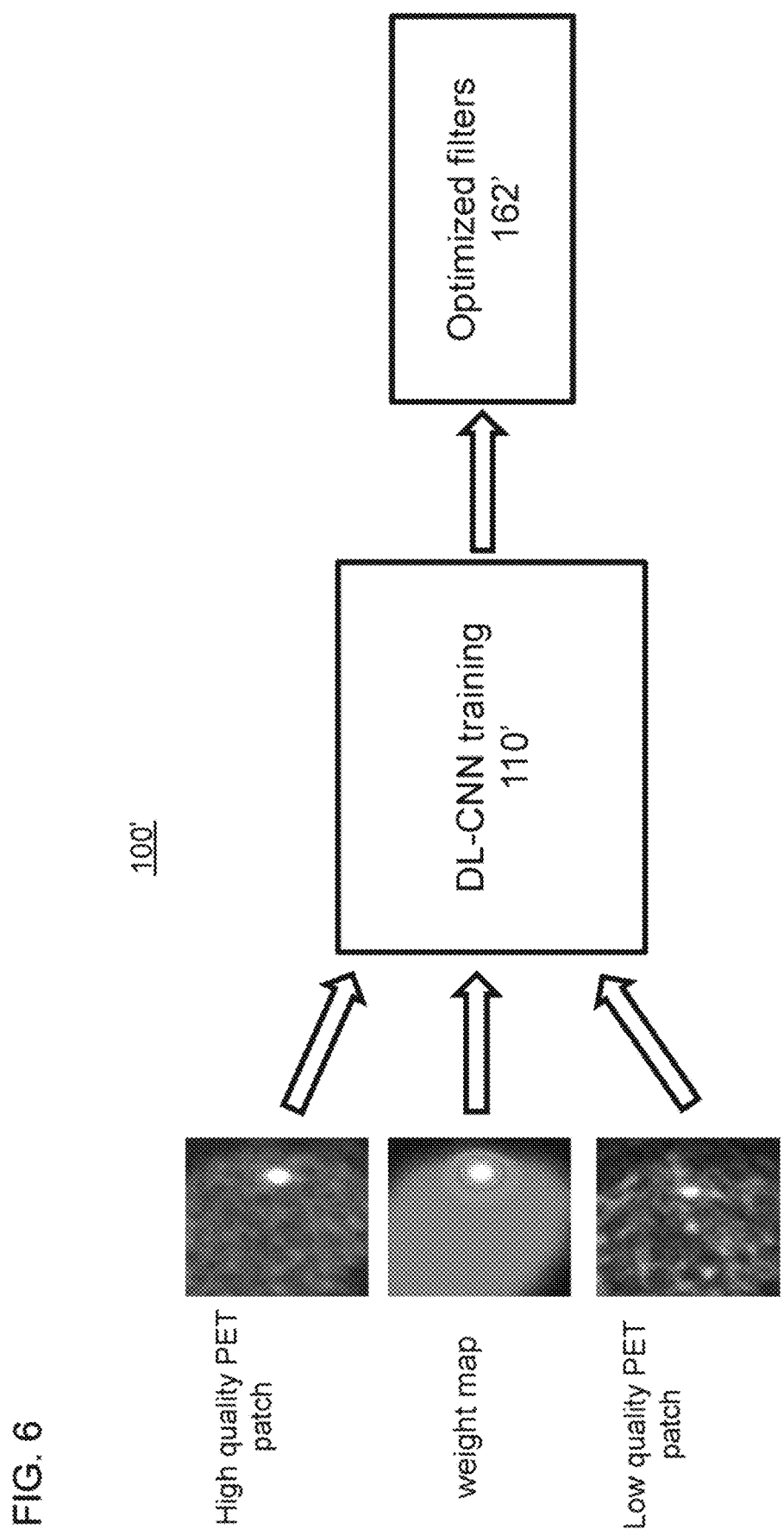
FIG. 6 shows a flow diagram a method 100', which is method 100 that has been modified to implement the feature-oriented training step 110', according to one implementation.

FIGS. 5 and 6 illustrate a feature-oriented method to improve training of the network 162. Although method 100 can be performed with training data that has not been labelled, better denoising results in method 200 can be achieved if the training data has been segmented and labeled/weighted to indicate those regions/features within the PET image that have greater clinical significance (e.g., the region of a lesion). Thus, the learned network can emphasize the image quality in the segmented regions deemed to have greater clinical significance by weighting the loss function to produce a denoised image that especially matches the high-quality images in the regions of interest (e.g., lesions).

The advantages of the supervision process 500 and the modified training step 110' (corresponding to a modified version of step 110) can be better understood by considering that, in general, denoising training does not require labelled data (e.g. segmenting and label a target object). This is because a default of uniform weighting can be applied to all voxels used in the training, such that the training tries to minimize the discrepancies between the denoised low-quality image (i.e., the low-quality image after it has been processed using the DL-CNN network) and the high-quality image. This training is realized by adjusting various network parameters to minimize a loss function that applies an equal weight to all voxel-wise differences in the image patches. However, since the signal of interest in PET images is often spatially small compared with the background (e.g., a lesion region can be much smaller than the background region), the large number of background voxels can dominate the loss-function calculation, guiding the network towards a solution that overemphasizes smoothing to remove noise backgrounds and underemphasizes the preservation of small features and fine detail in the smaller region of interest.

To counter balance this propensity, a feature-oriented denoising approach can be used to increase the weight applied to the region of the lesion during the training in step 110. As shown in FIG. 5, process 500 includes a segmentation step 510 to generate a lesion mask and a weight calculation step 520 to generate a weight map for each high-quality image in the training dataset. In certain implementations, the weight maps can be generated by manually segmenting the target lesions in the training dataset. In certain implementations, the weight maps can be automatically segmented (e.g., using a threshold and region growing method), and then user inputs can be used to identify which segmented regions are background and which are regions of interest. The weight maps have higher value in the lesions and lower value in the background, and they can be uniform for the patches that do not contain lesions. The weight map is used to compensate for the different number of voxels in the signal/lesion region and background region. This balances the competing objectives of learning to preserve desired small features while suppressing noise in the background.

In step 510 of process 500, lesions are identified and manually segmented to obtain lesion masks (also referred to as a region of interest mask) corresponding to a given high-quality PET image.

In step 520 of process 500, these masks are then used to create distance dependent weight maps (e.g., weights for lesion voxels are 1 and decreased to 0.1 for far away voxels). In certain implementations, a gradual reduction of weights can be used to provide a fuzzy boundary between to lesion voxels and the background voxels, thereby accounting for segmentation errors/uncertainties.

Then, in a modified training step 110', the weight map is used to a calculate a weighted loss function, such as $$L(\Theta) = \frac{1}{N} \sum_{i \in N} w \times \psi(F(y_i; \Theta) - (y_i - x_i)),$$

wherein W is the weight map, and the symbol "x" denotes pixel-wise multiplication.

A second non-limiting example is now provided to illustrate the advantages of using process 500 when training the network 162'. The network 162' can be the same as the network 162 and is applied the same in step 210, except that network 162' is trained using the weight map rather than uniform weighting in the loss function.

The five-layer residual network defined by Table 2 was trained with simulations and phantoms, and then was applied to the noisy reconstruction of a NEMA body phantom (shown on the left-hand-side of FIG. 7), which was reconstructed using an OS-EM reconstruction method.

TABLE 2

Architecture of the deep residual network for the first example.

| layer | Layer Functions | | |
|---|---|---|---|
| 1 | Conv | ReLU | |
| 2 | Conv | BN | ReLU |

TABLE 2-continued

Architecture of the deep residual network for the first example.

| layer | Layer Functions | | |
|---|---|---|---|
| 3 | Conv | BN | ReLU |
| 4 | Conv | BN | ReLU |
| 5 | Conv | | |

Figure 7:
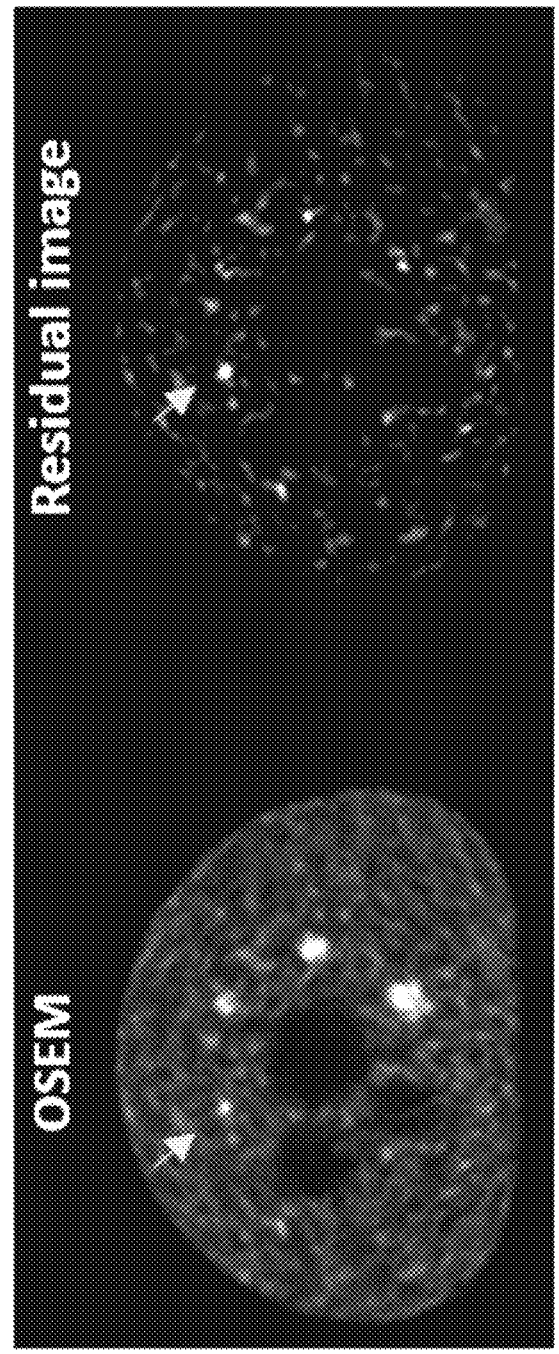
FIG. 7 shows, on the left-hand-side, an example of a slice of a noisy PET image that has been reconstructed using an ordered subsets (OS) expectation maximization (EM) algorithm, and, on the right-hand-side, shows an example of a residual determined from the noisy PET image by the DL-CNN network, according to one implementation.

FIG. 7 shows, for the second example, a reconstructed image on the left-hand-side and a residual image on the right-hand-side. The estimated residual image is shown on the right-hand-side of FIG. 7.

FIG. 7 shows that the smallest sphere (10 mm) is misclassified as noise and mostly removed/subtracted from the denoised image. This is due to the fact that this lesion only contains a few voxels and the feature is not visually obvious. Therefore, without sufficient training samples on images having similarly small features represented in the signal (as opposed to just in the noise), the convolutional neural network will favor mapping it as noise, because doing so reduces the global loss function.

In the second example, processes 500 and method 110' use a feature oriented learning approach that assigns different weights to different voxels in order to compensate for this discrepancy in the number of voxels in the region of interest versus in the background. To generate the weight maps, the lesions/regions of interest are first segmented in the target images (e.g., either manually or by thresholding) in order to create lesion masks, as illustrated in FIG. 5. The weight maps are generated from the lesion masks by assigning $N_b/N_1$ times higher weights in the lesions, where $N_b$ and $N_1$ are the total number of voxels in the background and the total number of voxels in the lesions, respectively. In other implementations, as would be understood by a person of ordinary skill in the art, other ratios and methods can be used to select the relative weight values between the background and the region of interest, without departing from the spirit of the weight mask. The background voxels can be set to unity in the weight map. The weight map is then convolved with a Gaussian kernel to accommodate the segmentation error. The weight map can be uniform for the patches that do not contain lesions. The weight map constrains the network to learn to preserve desired small features while suppressing noise in the background.

To evaluate the improvements realized using the above-described weight map, the network was trained with a training dataset that includes images of a computer-simulated phantom, and images of two physical phantoms. The simulated phantom images were generated from an activity map with spheres of various size and contrast and different acquisition durations (e.g., 1, 2, 3 and 4 min) were simulated to generate different noise levels. The high quality target images were simulated with 10-min acquisition. Altogether the training dataset includes twelve datasets. Two networks were trained using the same architecture and training datasets: (i) a DL-CNN trained using method 110, i.e., with a uniform weighting (i.e., without weight maps), and (ii) a DL-CNN trained using method 110', i.e., with weight maps, as described above. For DL-CNN trained using weight maps, the lesion masks were generated by applying thresholding to the target images followed by convolution with a Gaussian kernel.

Figure 8A:
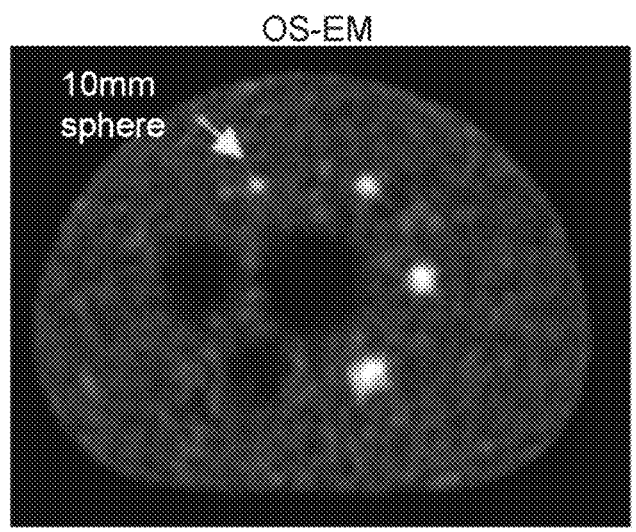
FIG. 8A shows another example of a noisy PET image that has been reconstructed using an OS-EM algorithm, according to one implementation.
Figure 8B:
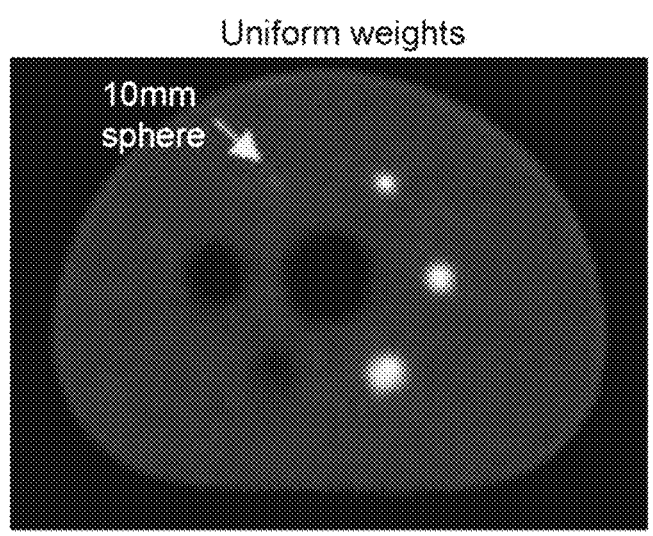
FIG. 8B shows another example of a denoised PET image obtained using a DL-CNN network that was trained using uniform weights in the loss function, according to one implementation.
Figure 8C:
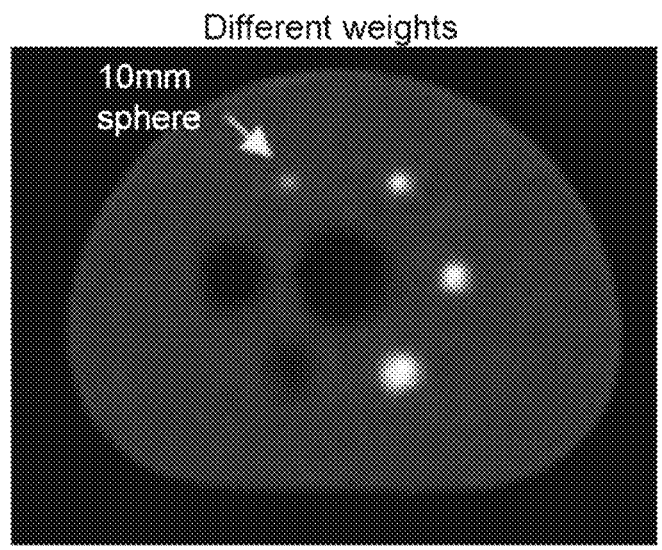
FIG. 8C shows an example of another denoised PET image obtained using a DL-CNN network that was trained using the feature-oriented training step 110' in which weight maps are applied in the loss function, according to one implementation.

To evaluate the improvements due to training with weight maps, the two trained networks described above were applied to an OS-EM reconstructed image of a standard NEMA phantom (2 mCi) that was scanned for 2 minutes (the NEMA Phantom was not included in training dataset). The OS-EM reconstructed image is shown without denoising in FIG. 8A. FIGS. 8B and 8C show the same image after denoising with a DL-CNN network trained using a uniform weighting in the loss function and a DL-CNN network trained using different weights provided by the weight maps, respectively.

TABLE 3

Results of a coefficient of variation analysis performed on denoised images obtained by denoising an OS-EM reconstructed image by applying DL-CNN networks using either a uniform weighting or different weights determined by weight maps.

| Sphere | OSEM | Uniform weighting | Different weights |
|---|---|---|---|
| 10 mm | 52 | 12 | 32 |
| 13 mm | 72 | 65 | 65 |
| 17 mm | 86 | 77 | 77 |
| 22 mm | 80 | 77 | 81 |

The denoised images were then assessed by measuring contrast recovery of each sphere and coefficient of variation of the background. The results of this analysis are shown in Table 3. For large features, such as those corresponding to the 22 mm sphere, the features are preserved in the denoised image regardless of whether the training data is weighted or uniform. That is, the coefficient of variation for denoising by a DL-CNN network is largely independent of whether the DL-CNN network was trained using a uniform weighting or trained using different weights provided by the weight maps. However, the DL-CNN network trained using the different weights of the weight maps performs much better for preserving fine features in the denoised image (e.g., features corresponding to the 10 mm sphere), whereas the DL-CNN network trained using a uniform weighting tends to identify these fine features as noise and mostly filters them out the denoised image.

Now, a modified training method 110" is described with reference to FIG. 9. In certain implementations, methods 100 and 200 can use other medical images. Often other modalities of medical imaging can produce higher resolution images than the corresponding PET image. These other medical images can be used to correct for partial volumes, in which a voxel in the PET image is at a border between two different types of material (e.g., by straddling the boundary between a lesion, which has a high level of activity, and surrounding organs, which have a lower level of activity). When the other image has a higher resolution than the PET image and can be used to identify the two (or more) different types material/organs partially occupying a given voxel in the PET image, then the other medical image can be used to perform a partial volume correction. Any type of other medical image can be used. As a non-limiting example, the discussion herein assumes (unless stated otherwise) that the other medical image is a CT image.

Figure 9:
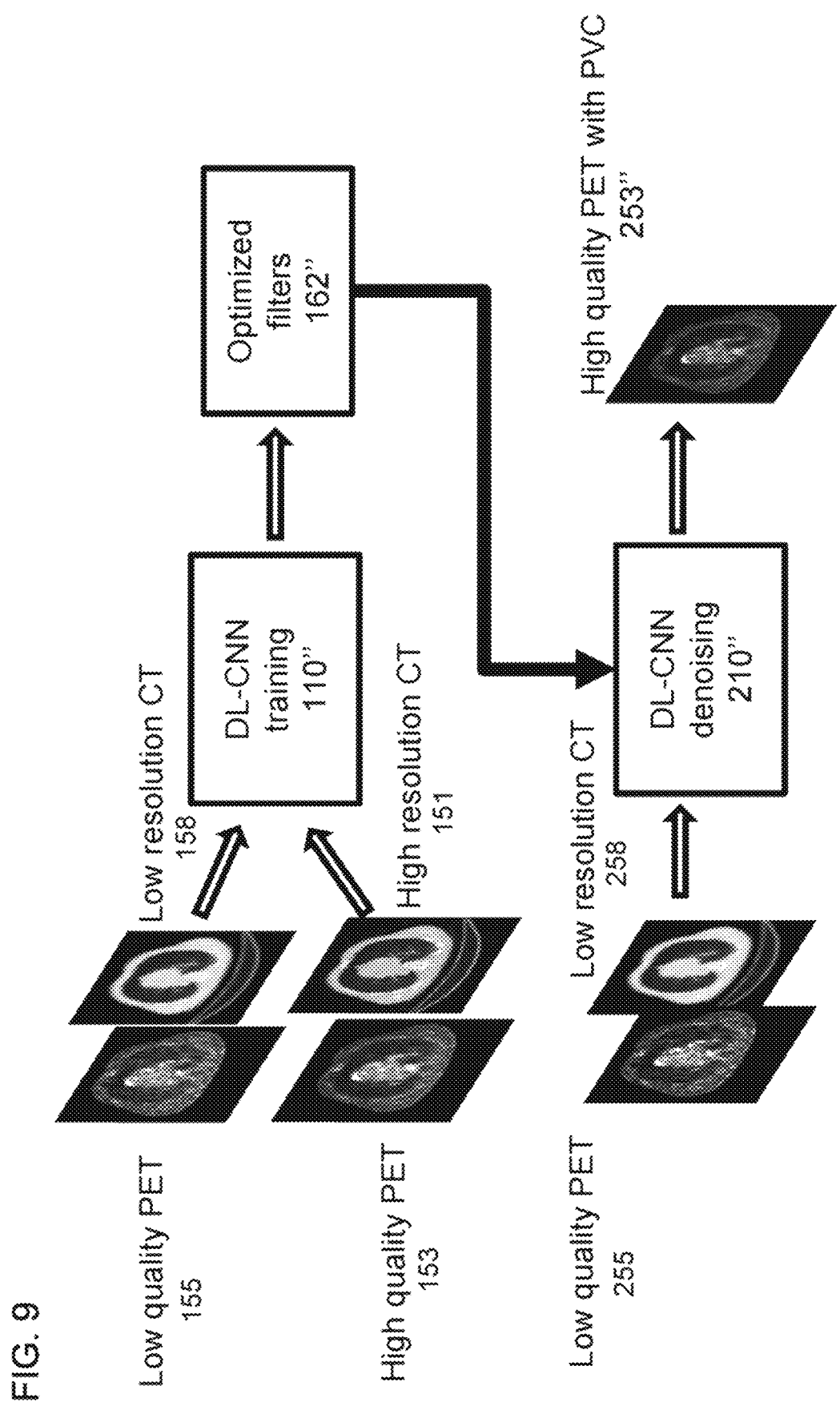
FIG. 9 shows implementations steps 110" and 210" that are modified versions of steps 110 and 210 that use other medical images to correct for partial volume effects (PVE), according to one implementation.

FIG. 9 show a flow diagram of a modified implementation of methods 100 and 200, in which the step 110" trains a modified network 162" and step 210" applies a low-quality PET image 255 and low-quality CT image 258 to the modified network 162". That is, steps 110" and 210" use a combination of a low-quality PET image and a low-quality CT image (or other non-PET image) to generate a high-quality PET image with PVC 253". As discussed above, in PET imaging, the image quality can be degraded by partial volume effects (PVE), e.g., due to the limited intrinsic system resolution. That is, coarse graining due to large voxels in the PET image can result in PVE, which introduces spill-over of activity into neighboring regions and reduces image resolution and contrast. To mitigate the PVE, the modified methods 100 and 200 incorporate high resolution anatomical information obtained from CT (or MRI) imaging into the DL-CNN network 162" to correct for PVE in the PET images. As shown in FIG. 8, a high-resolution CT (MRI) image can be acquired and reconstructed in tandem to with the PET image. The reconstructed CT (MRI) image can then be forward projected using the PET system geometry, and then a second CT (MRI) image can be reconstructed from the forward projection images using the same PET reconstruction protocol. The result is a CT image at the PET resolution (i.e., a resolution degraded CT image), which is labeled in FIG. 9 as a low-resolution CT image 158. Alternatively, an attenuation map used in PET reconstruction can be used to approximate the resolution degraded CT image 158.

In step 110", the low quality PET image 155 and the low-resolution CT image 158 are dual-channel inputs applied to the network 162", and the loss function is calculated by comparing the low-quality PET image 155 and low-resolution CT image 158 to the respective high-quality PET image 153 and high-resolution CT image 151. The objective is to teach the network to learn denoising from the low/high quality PET pairs, and resolution enhancement from the low/high-resolution CT pairs.

In step 210", the trained network 162" is applied to a combination of a low-quality PET image together with a low-resolution CT (MRI) image obtained in a clinical setting in order to obtain the high-quality PET image with PVC 253".

Figure 10:
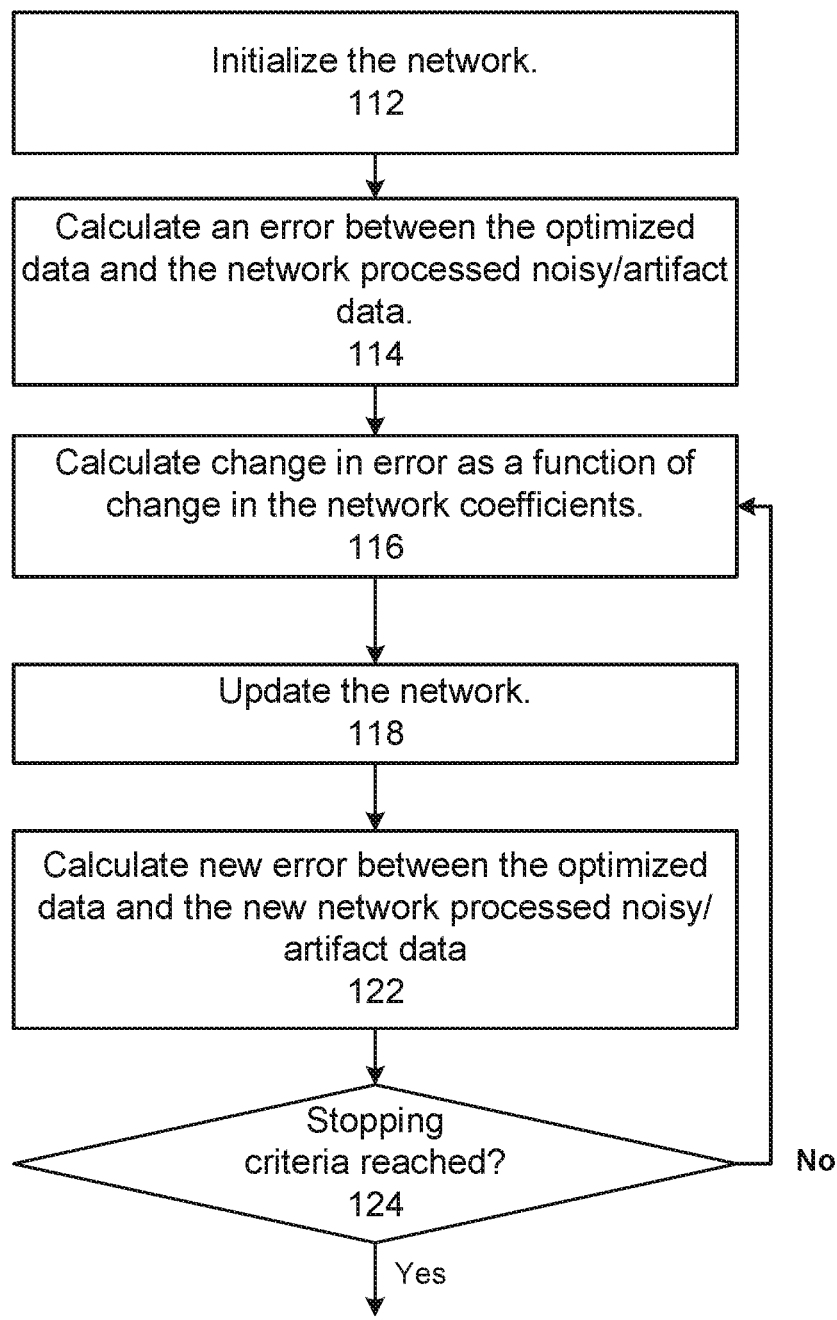
FIG. 10 shows an example of a flow diagram for training a DL-CNN network, according to one implementation.

Now a more detailed description of step 110 is provided. This description can be generalized to the modified versions of step 110 (e.g., step 110' and step 110"), as would be understood by a person of ordinary skill in the art. FIG. 10 shows a flow diagram of one implementation of the training step 110 performed during method 100. In step 110 of method 100, low-quality (e.g., noisy) data 155 and high-quality (e.g., optimized) data 153 are used as training data to train a DL-CNN network, resulting in the DL-CNN network being output from step 124. The term "data" here can refer to an image. More generally, data 155 can be referred to as defect-exhibiting data, for which the "defect" can be any undesirable characteristic that can be affected through image processing (e.g., noise or an artifact). Similarly, data 153 can be referred to as defect-reduced data, defect-minimized data, or optimized data, for which the "defect" is less than in the data 155. In an example using reconstructed images for data 155 and 153, the offline DL training method 100 trains the DL-CNN network 162 using a large number of noisy reconstructed images 155 that are paired with corresponding high-image-quality images 153 to train the DL-CNN network 162 to produce images resembling the high-image-quality images from the noisy reconstructed images.

In step 110 a set of training data is obtained, and the network 162 is iteratively updated to reduce the error (e.g., the value produced by a loss function), such that the noisy data 115 processed by the DL-CNN network closely matches the optimized data 153. In other words, DL-CNN network infers the mapping implied by the training data, and the cost function produces an error value related to the mismatch between the optimized data 153 and the denoised data produced by applying a current incarnation of the DL-CNN network 162 to the noisy data 115. For example, in certain implementations, the cost function can use the mean-squared error to minimize the average squared error. In the case of a of multilayer perceptrons (MLP) neural network, the backpropagation algorithm can be used for training the network by minimizing the mean-squared-error-based cost function using a (stochastic) gradient descent method.

Training a neural network model essentially means selecting one model from the set of allowed models (or, in a Bayesian framework, determining a distribution over the set of allowed models) that minimizes the cost criterion (i.e., the error value calculated using the cost function). Generally, the DL-CNN network can be trained using any of numerous algorithms for training neural network models (e.g., by applying optimization theory and statistical estimation).

For example, the optimization method used in training the DL-CNN 162 can use some form of gradient descent incorporating backpropagation to compute the actual gradients. This is done by taking the derivative of the cost function with respect to the network parameters and then changing those parameters in a gradient-related direction. The backpropagation training algorithm can be: a steepest descent method (e.g., with variable learning rate, with variable learning rate and momentum, and resilient backpropagation), a quasi-Newton method (e.g., Broyden-Fletcher-Goldfarb-Shanno, one step secant, and Levenberg-Marquardt), or a conjugate gradient method (e.g., Fletcher-Reeves update, Polak-Ribiére update, Powell-Beale restart, and scaled conjugate gradient). Additionally, evolutionary methods, such as gene expression programming, simulated annealing, expectation-maximization, non-parametric methods and particle swarm optimization, can also be used for training the DL neural networks 162.

FIG. 10 shows a non-limiting example of a flow diagram of an implementation of step 110 of method 100 for training the network using the training data. The data 115 in the training data can be a noisy image or an image exhibiting an artifact. For example, an artifact can arise from a particular method of reconstruction, or arise from a method used for acquiring the emission data.

In step 112 of step 110, an initial guess is generated for the coefficients of the DL-CNN network 162. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 114 through 124 provide a non-limiting example of an optimization method for training the DL-CNN.

In step 114 of step 110, an error is calculated (e.g., using a loss function or a cost function) to represent a measure of the difference (e.g., a distance measure) between the optimized data 153 (i.e., ground truth) and noisy data 115 after applying a current version of the network 162. The error can be calculated using any known cost function or distance measure between the image data, including those cost functions described above. Further, in certain implementations the error/loss function can be calculated using one or more of a hinge loss and a cross-entropy loss.

Additionally, the loss function can be combined with a regularization approach to avoid overfitting the network to the particular instances represented in the training data. Regularization can help to prevent overfitting in machine learning problems. If trained too long, and assuming the model has enough representational power, the network will learn the noise specific to that dataset, which is referred to as overfitting. In case of overfitting, the DL-CNN becomes a poor generalization, and the variance will be large because the noise varies between datasets. The minimum total error occurs when the sum of bias and variance are minimal. Accordingly, it is desirable to reach a local minimum that explains the data in the simplest possible way to maximize the likelihood that the trained network represents a general solution, rather than a solution particular to the noise in the training data. This goal can be achieved, e.g., by early stopping, weight regularization, lasso regularization, ridge regularization, or elastic net regularization.

In certain implementations, the network 162 is trained using backpropagation. Backpropagation can be used for training neural networks and is used in conjunction with gradient descent optimization methods. During a forward pass, the algorithm computes the network's predictions based on the current parameters $\theta$. These predictions are then input into the loss function, by which they are compared to the corresponding ground truth labels (i.e., the high quality image 153). During the backward pass, the model computes the gradient of the loss function with respect to the current parameters, after which the parameters are updated by taking a step of size of a predefined size in the direction of minimized loss (e.g., in accelerated methods, such that the Nesterov momentum method and various adaptive methods, the step size can be selected to more quickly converge to optimize the loss function).

The optimization method by which the backprojection is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, e.g, Nesterov momentum technique or an adaptive method, such as Adagrad sub-gradient method, an Adadelta or RMSProp parameter update variation of the Adagrad method, and an Adam adaptive optimization technique. The optimization method can also apply a second order method by incorporating the Jacobian matrix into the update step.

The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to the non-limiting example shown in FIG. 10, step 116 of step 110 determines a change in the error as a function of the change in the network can be calculated (e.g., an error gradient), and this change in the error can be used to select a direction and step size for a subsequent change to the weights/coefficients of the DL-CNN network 162. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 118 of step 110, a new set of coefficients are determined for the DL-CNN network 162. For example, the weights/coefficients can be updated using the changed calculated in step 116, as in a gradient descent optimization method or an over-relaxation acceleration method.

In step 122 of step 110, a new error value is calculated using the updated weights/coefficients of the DL-CNN network 162.

In step 124 of step 110, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in step 110 will continue back to the start of the iterative loop by returning and repeating step 116 using the new weights and coefficients (the iterative loop includes steps 116, 118, 122, and 124). When the stopping criteria are satisfied the training process performed in step 110 is completed.

Figure 11:
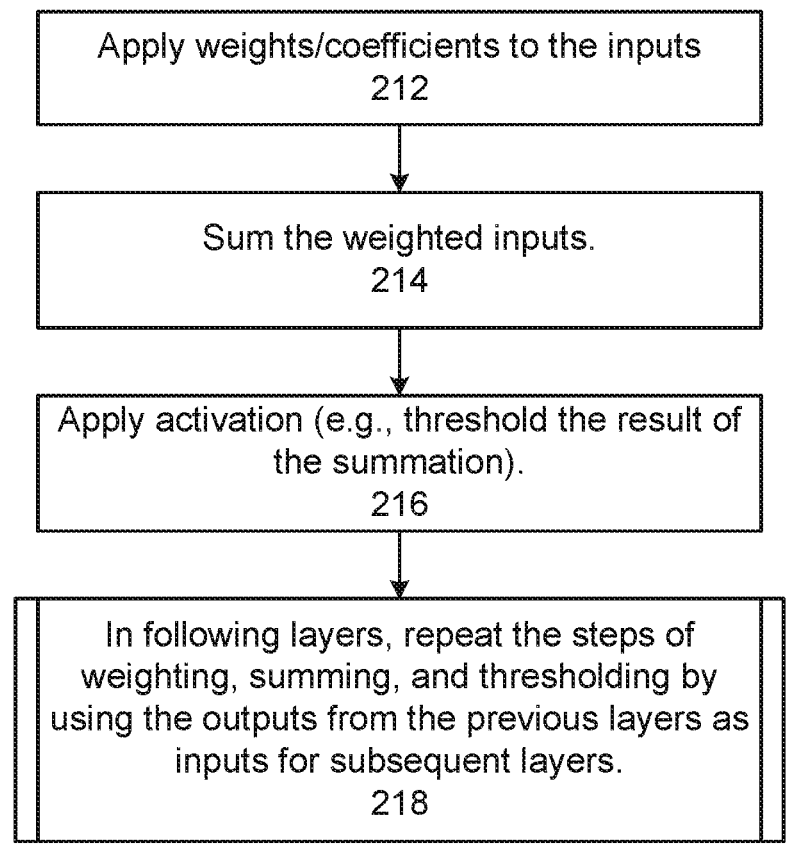
FIG. 11 shows an example of a flow diagram for applying a general the artificial neural network (ANN), according to one implementation.
Figure 12:
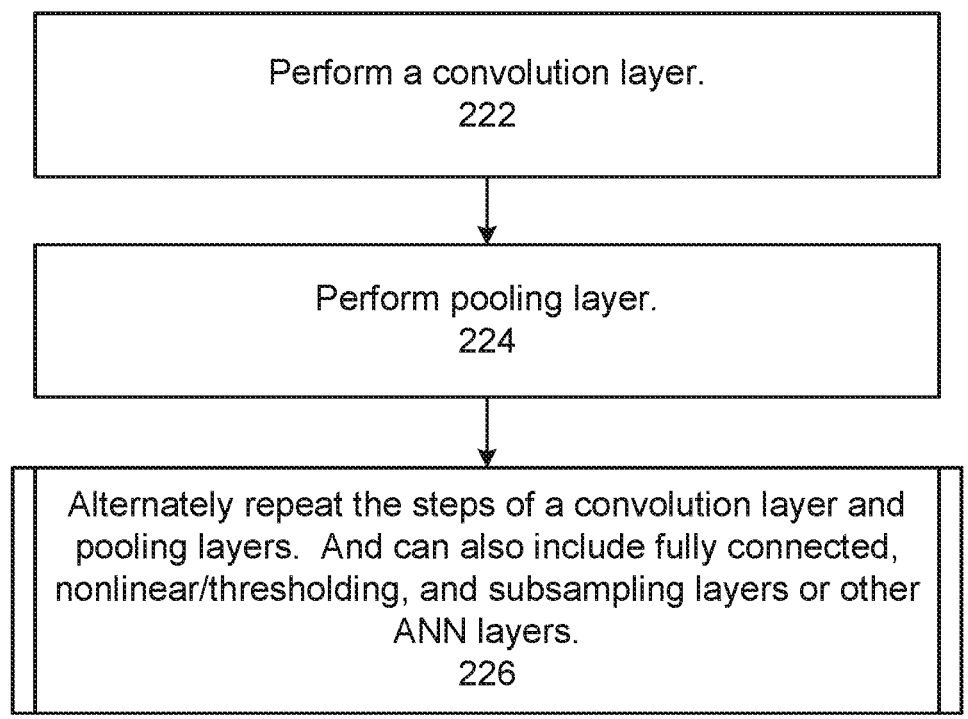
FIG. 12 shows an example of a flow diagram for applying a convolutional neural network (CNN), according to one implementation.

FIGS. 11 and 12 show flow diagrams of implementations of step 210. FIG. 11 is general for any type of layer in a feedforward artificial neural network (ANN), including, e.g., fully connected layers, whereas FIG. 12 is specific to convolutional and pooling layers in a CNN. The DL-CNN can include both fully connected layers and convolutional and pooling layers, resulting in flow diagram that is a combination of FIGS. 11 and 12, as would be understood by a person of ordinary skill in the art. The implementations of step 210 shown in FIGS. 11 and 12 also correspond to applying the DL-CNN network 162 to the respective images of the training dataset during step 110.

In step 212, the weights/coefficients corresponding to the connections between neurons (i.e., nodes) are applied to the respective inputs corresponding to the pixels of the reconstructed image.

In step 214, the weighted inputs are summed. When the only non-zero weights/coefficients connecting to a given neuron on the next layer are regionally localized in an image represented in the previous layer, the combination of steps 212 and 214 is essentially identical to performing a convolution operation.

In step 216, respective thresholds are applied to the weighted sums of the respective neurons.

In process 218 the steps of weighting, summing, and thresholding are repeated for each of the subsequent layers.

FIG. 12 show a flow diagram of another implementation of step 210. The implementation of step 210 shown in FIG. 12 corresponds to operating on the reconstructed image using a non-limiting implementation of the DL-CNN network 162.

In step 222, the calculations for a convolution layer are performed as discussed in the foregoing and in accordance with the understanding of convolution layers of one of ordinary skill in the art.

In step 224, the outputs from the convolution layer are the inputs into a pooling layer that is performed according to the foregoing description of pooling layers and in accordance with the understanding of pooling layers of one of ordinary skill in the art.

In process 226 the steps of a convolution layer followed by a pooling can be repeated a predefined number of layers. Following (or intermixed with) the convolution and pooling layers, the output from a pooling layer can be fed to a predefined number of ANN layers that are performed according to the description provided for the ANN layers in FIG. 11. The final out will be a reconstructed image having the desired noise/artifact free characteristics.

Figure 13A:
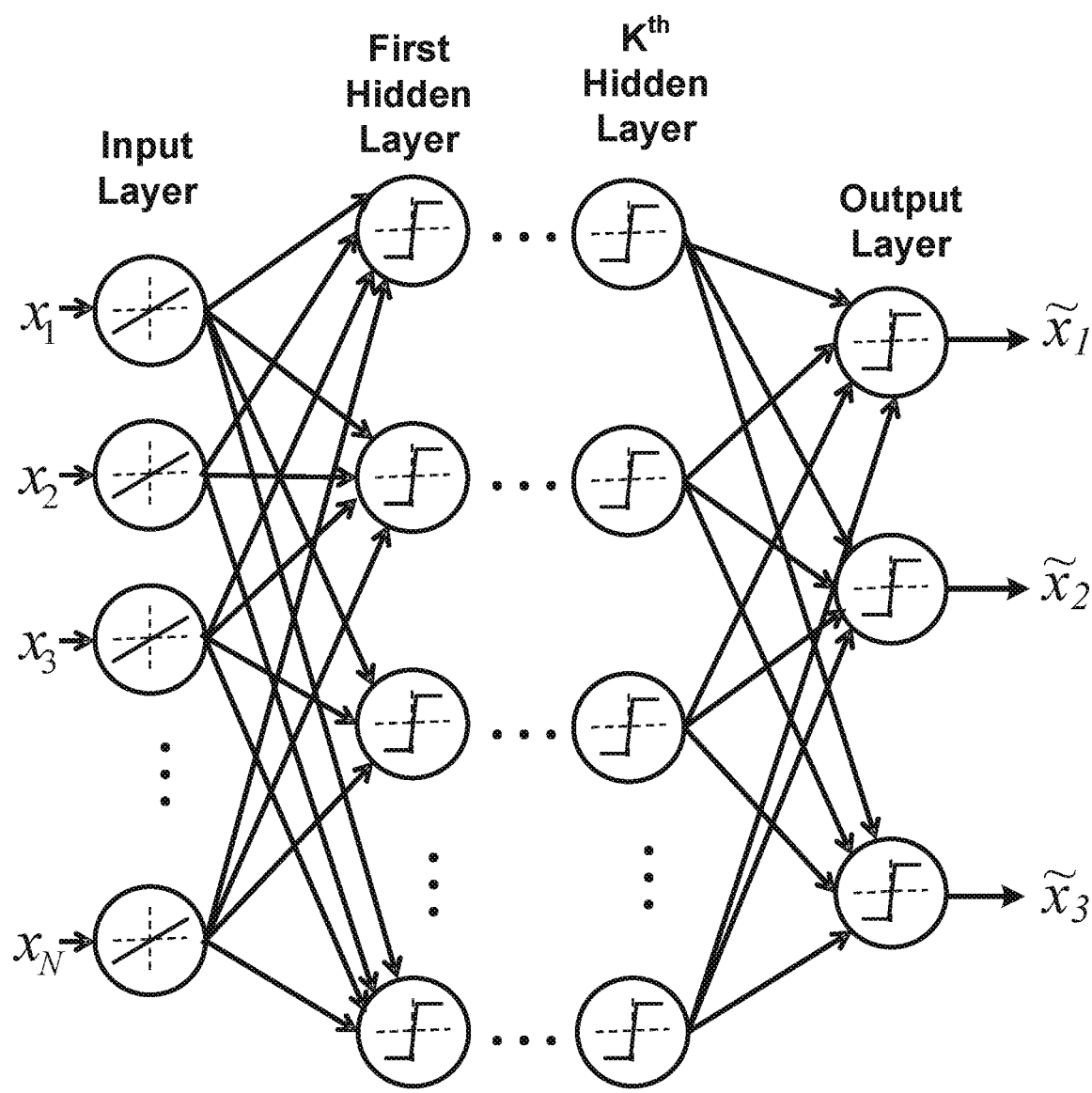
FIG. 13A shows an example of a feedforward ANN, according to one implementation.
Figure 13B:
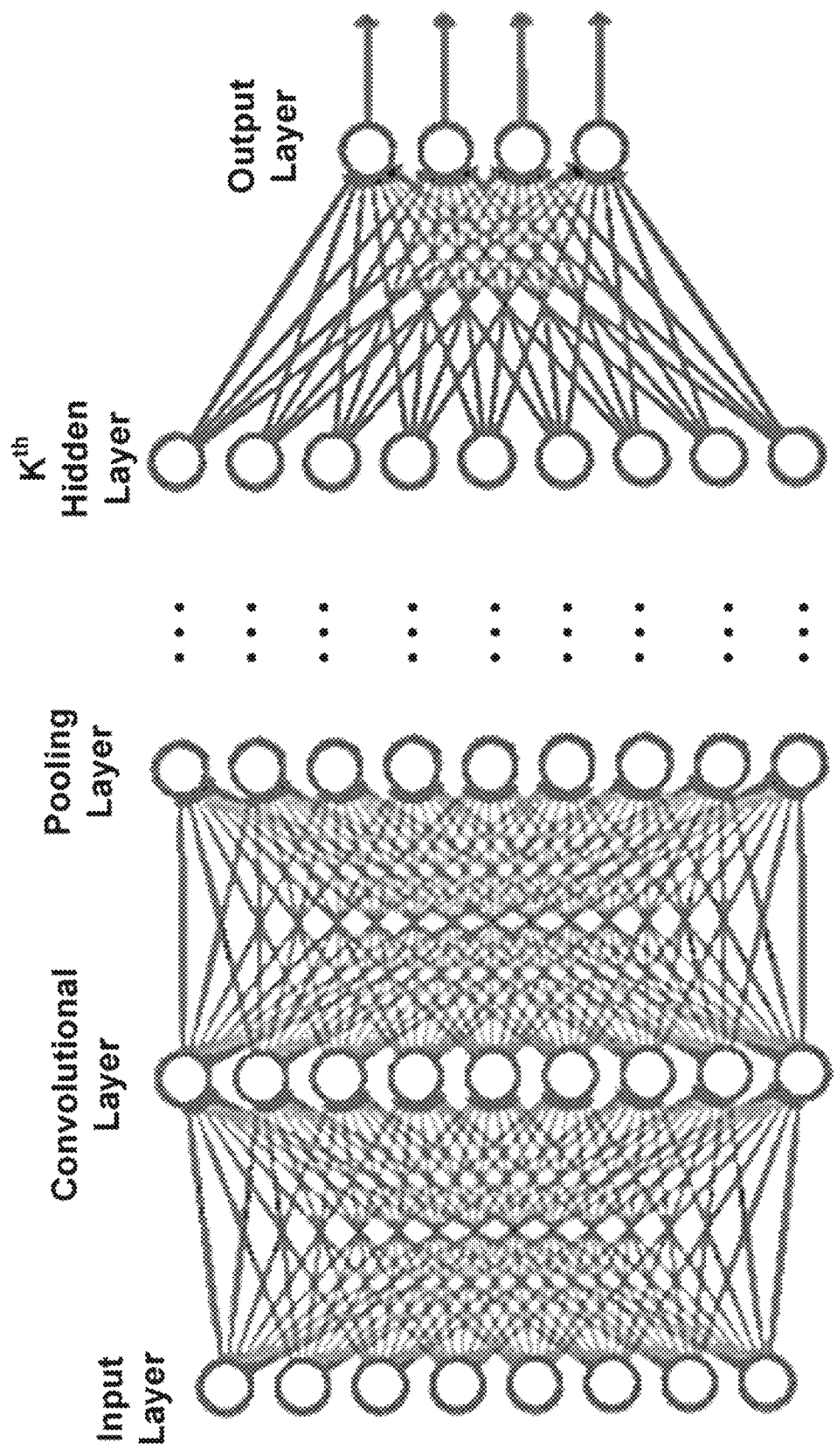
FIG. 13B shows an example of a CNN, according to one implementation.
Figure 13C:
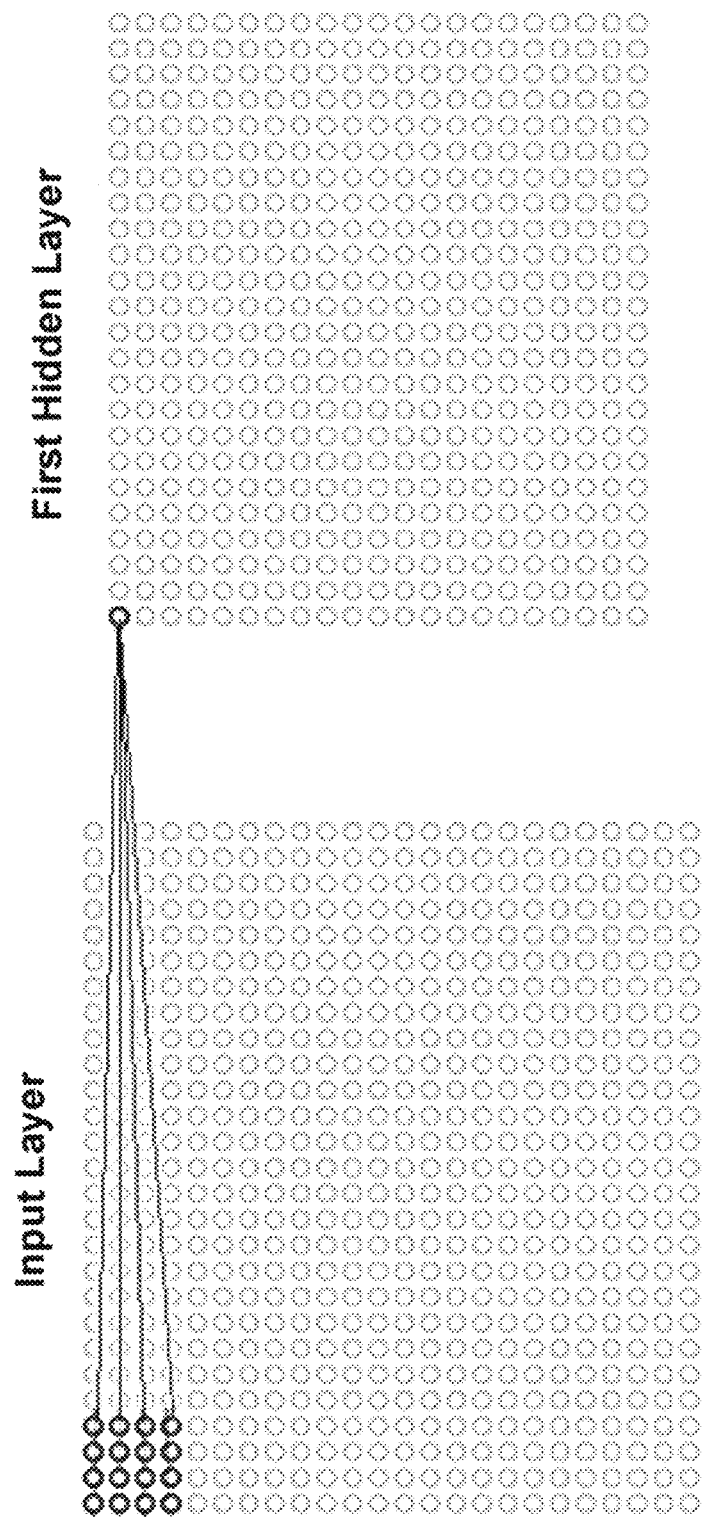
FIG. 13C shows an example of implementing a convolution layer for one neuronal node of the convolution layer, according to one implementation.

FIGS. 13A, 13B, and 13C show various examples of the inter-connections between layers in the DL-CNN network 162. The DL-CNN network 162 can include fully connected, convolutional, and the pooling layer, all of which are explained below. In certain preferred implementations of the DL-CNN network 162, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL-CNN network 162 can also incorporate batch normalization, as also exemplified in the first and second examples discussed above.

FIG. 13A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers, and is called an autoencoder. The DL-CNN network 162 can have more than three layers of neurons, and has as many outputs neurons $\tilde{x}_N$ as input neurons, wherein N is the number of pixels in the reconstructed image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the inter-connections, and (iii) the activation function that converts a neuron's weighted input to its output activation.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIG. 13. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 13A (and similarly in FIG. 13B), the neurons (i.e., nodes) are depicted by circles around a threshold function. For the non-limiting example shown in FIG. 13A, the inputs are depicted as circles around a linear function, and the arrows indicate directed connections between neurons. In certain implementations, the DL-CNN network 162 is a feedforward network as exemplified in FIGS. 2A and 2B (e.g., it can be represented as a directed acyclic graph).

The DL-CNN network 162 operates to achieve a specific task, such as denoising a CT image, by searching within the class of functions F to learn, using a set of observations, to find m*∈F which solves the specific task in some optimal sense (e.g., the stopping criteria used in step 124 of step 110 discussed above). For example, in certain implementations, this can be achieved by defining a cost function C:F→□ such that, for the optimal solution m*, C(m*)≤C(m)∀m∈F (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data).

FIG. 13B shows a non-limiting example in which the DL-CNN network 162 is a convolutional neural network (CNN). CNNs are type of ANN that has beneficial properties for image processing, and, therefore, have specially relevancy for the applications of image denoising. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

FIG. 13C shows an example of a 4×4 kernel being applied to map values from an input layer representing a two-dimensional image to a first hidden layer, which is a convolution layer. The kernel maps respective 4×4 pixel regions to corresponding neurons of the first hidden layer.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolutional layers, which means that the same filter (weights bank) is used as the coefficients for each pixel in the layer; this both reduces memory footprint and improves performance. Compared to other image-processing methods, CNNs advantageously use relatively little pre-processing. This means that the network is responsible for learning the filters that in traditional algorithms were hand-engineered. The lack of dependence on prior knowledge and human effort in designing features is a major advantage for CNNs.

Figure 14A:
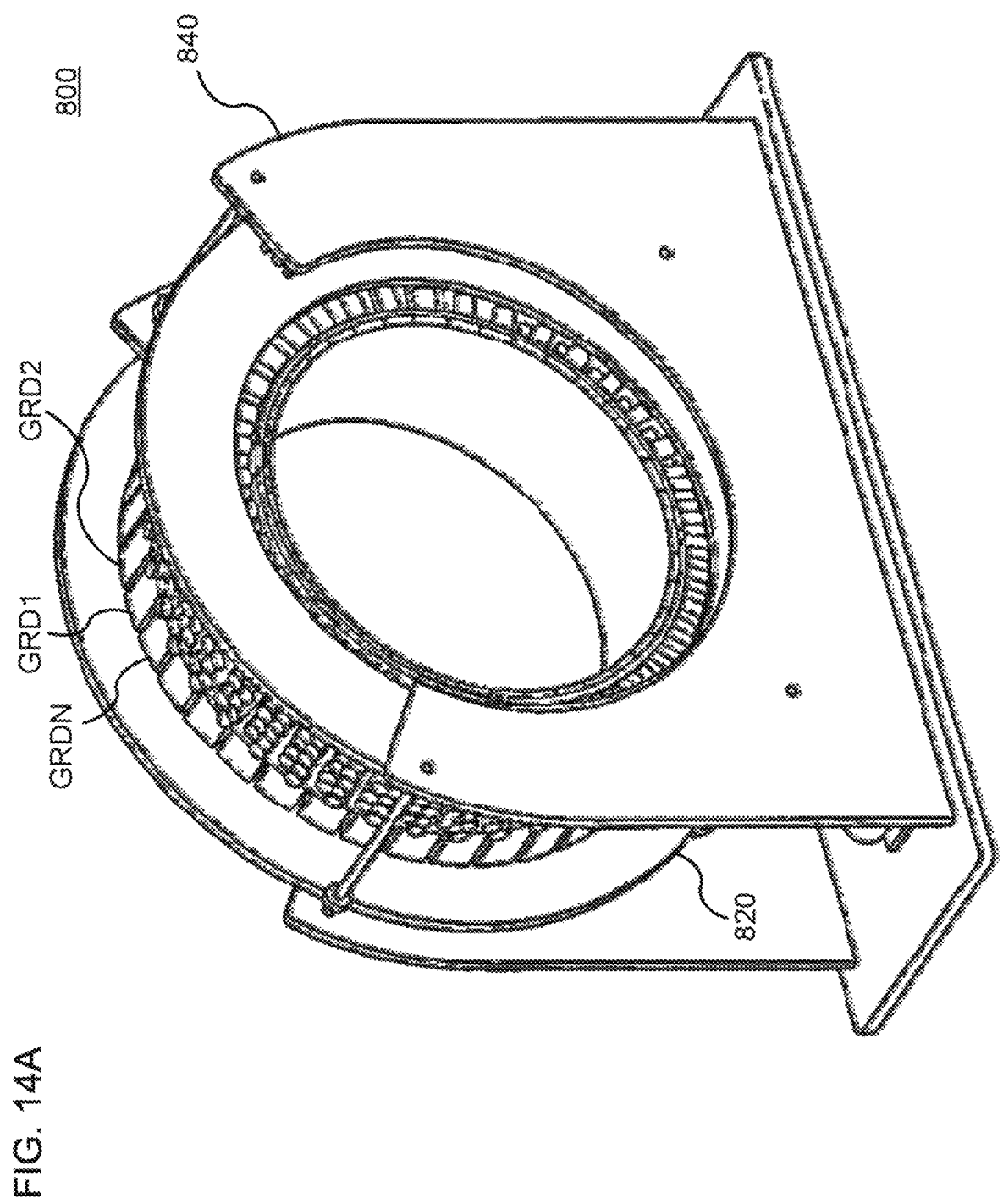
FIG. 14A shows a perspective view of a positron-emission tomography (PET) scanner, according to one implementation.
Figure 14B:
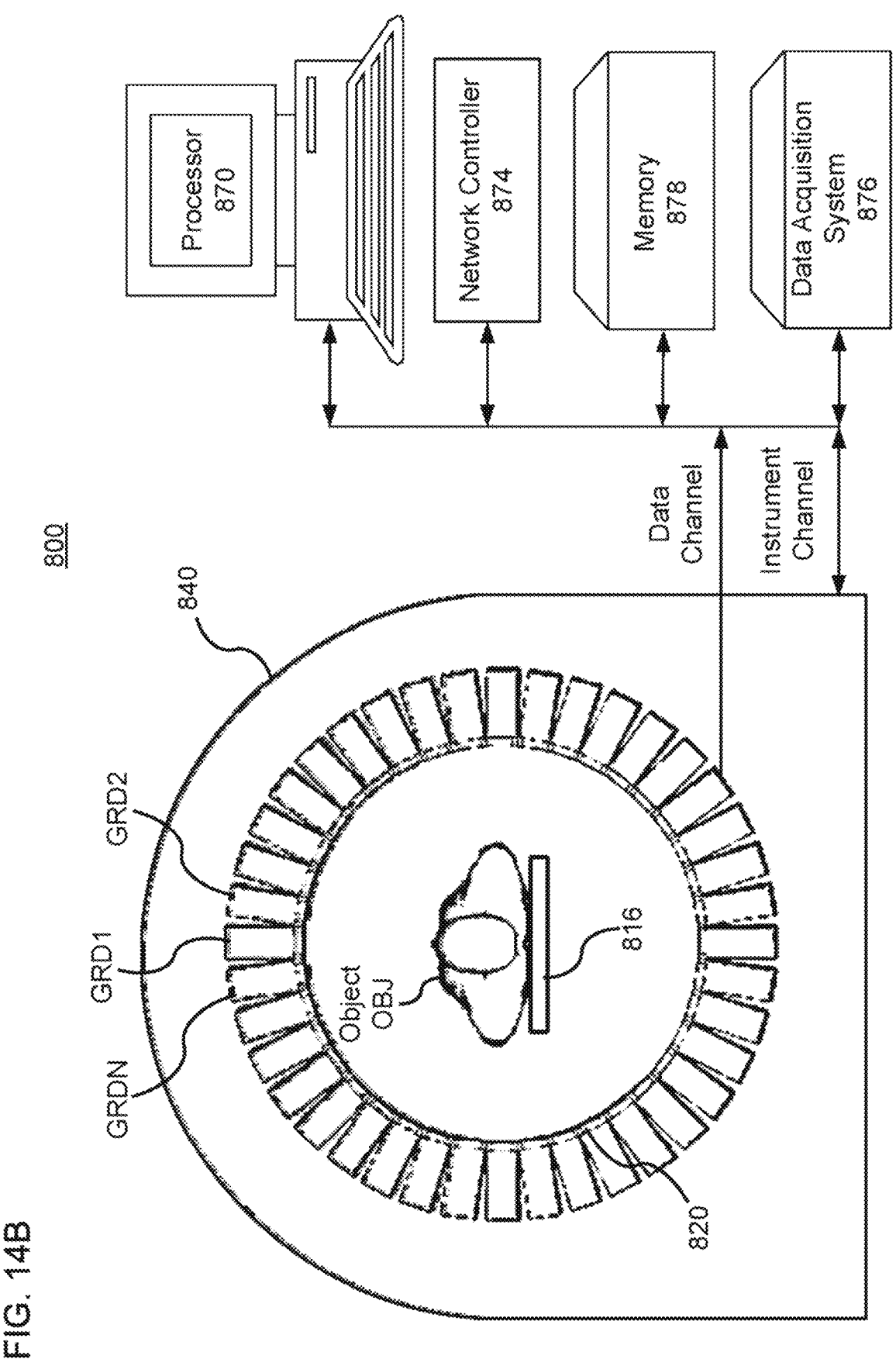
FIG. 14B shows a schematic view of the PET scanner, according to one implementation.

FIGS. 14A and 14B show a non-limiting example of a PET scanner 800 that can implement the methods 100 and 200. The PET scanner 800 includes a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 800.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs.

Alternatively, the scintillation photons can be detected by an array a silicon photomultipliers (SiPMs), and each individual detector crystals can have a respective SiPM.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 14B shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 14A and 14B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 14B shows an example of the arrangement of the PET scanner 800, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to the gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

In FIG. 14B, circuitry and hardware is also shown for acquiring, storing, processing, and distributing gamma-ray detection data. The circuitry and hardware include: a processor 870, a network controller 874, a memory 878, and a data acquisition system (DAS) 876. The PET imager also includes a data channel that routes detection measurement results from the GRDs to the DAS 876, a processor 870, a memory 878, and a network controller 874. The data acquisition system 876 can control the acquisition, digitization, and routing of the detection data from the detectors. In one implementation, the DAS 876 controls the movement of the bed 816. The processor 870 performs functions including reconstructing images from the detection data, pre-reconstruction processing of the detection data, and post-reconstruction processing of the image data, as discussed herein.

The processor 870 can be configured to perform various steps of methods 100 and/or 200 described herein and variations thereof. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform various steps of method 100 and/or method 200, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 878 can be a hard disk drive, CD-ROM drive, DVD drive, FLASH drive, RAM, ROM or any other electronic storage known in the art.

The network controller 874, such as an Intel Ethernet PRO network interface card from Intel Corporation of America, can interface between the various parts of the PET imager. Additionally, the network controller 874 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
processing circuitry configured to
acquire a reconstructed positron emission tomography (PET) image, the reconstructed PET image being reconstructed from emission data representing coincidence counts of respective pairs of gamma rays arising from electron-positron annihilation events, the coincidence counts being detected at a plurality of detector elements,
acquire a neural network including weighting coefficients of connections between neuronal nodes of respective layers of a plurality of layers between an input layer and an output layer of the neural network, the neural network having been trained using a training dataset that, for a given defect-minimized reconstructed data, includes two or more defect-exhibiting reconstructed data having greater defect levels than in the defect-minimized reconstructed data, the two or more defect-exhibiting reconstructed data being reconstructed using respective subsets of different sizes of a full PET dataset used to reconstruct the given defect-minimized reconstructed data, the training of the neural network including optimizing a loss function representing respective differences between the given defect-minimized reconstructed data and each of the two or more defect-exhibiting reconstructed data, and
apply the reconstructed PET image to the acquired neural network to generate a defect reduced image.

2. The apparatus according to claim 1, wherein the processing circuitry is further configured to
reconstruct the PET image using a same reconstruction method that was used to reconstruct the two or more defect-exhibiting reconstructed data and the given defect-minimized reconstructed data of the training dataset used to train the acquired neural network, and
acquire the neural network wherein the neural network has been trained using the two or more defect-exhibiting reconstructed data that are reconstructed using respective subsets of a full PET dataset used to reconstruct the given defect-minimized reconstructed data, each of the respective subsets including a different predefined amount or percentage of the full PET dataset.

3. The apparatus according to claim 1, wherein the processing circuitry is further configured to acquire the neural network wherein the neural network has been trained using a plurality of defect-minimized reconstructed data, each of the plurality of defect-minimized reconstructed data being paired with each of two or more defect-exhibiting reconstructed data that are respectively generated by reconstructing PET images using different sized subsets of the respective full PET emission dataset that is used to reconstruct the each of plurality of defect-minimized reconstructed data,
the different sized subsets are selected to produce the two or more defect-exhibiting reconstructed data that span a predefined range of statistical properties corresponding to images reconstructed based on PET scans performed using the plurality of detector elements, and,
when the reconstructed image to which the acquired neural network is applied is within the predefined range of statistical properties, an image quality of the defect reduced image is less affected by statistical properties of the reconstructed PET image than if the defect reduced image were generated using a neural network trained using defect-exhibiting reconstructed data that all had a same value for the statistical properties.

4. The apparatus according to claim 1, wherein the processing circuitry is further configured to apply the reconstructed PET image to the acquired neural network without adjustments based on statistical properties of the reconstructed PET image.

5. The apparatus according to claim 1, wherein the processing circuitry is further configured to acquire the neural network wherein the neural network has been trained to provide a same image quality for the defect reduced image independently of a defect level of the reconstructed PET image by the acquired neural network being trained to optimize the loss function simultaneously for the two or more defect-exhibiting reconstructed data having different noise levels that spans a predefined range of defect levels corresponding to images reconstructed based on PET scans using the plurality of detector elements.

6. The apparatus according to claim 1, wherein the processing circuitry is further configured to train the neural network in advance of the emission data being detected at the plurality of detector elements by obtaining the training dataset for training a neural network, the training dataset including a plurality of defect-minimized PET images respectively paired with two or more corresponding defect-exhibiting images of a plurality of defect-exhibiting PET images having various defect levels that are greater than a defect level of the corresponding defect-minimized image, wherein, for each of the plurality of defect-minimized PET images, the defect-minimized PET image is reconstructed using a respective full PET emission dataset, and the two or more corresponding defect-exhibiting images are reconstructed from different sized subsets of the respective full PET emission dataset that are selected to provide a range of defect levels among the two or more corresponding defect-exhibiting images, and training the neural network by iteratively adjusting tunable parameters of the neural network to minimize a loss function representing a difference between a respective defect-minimized image and an output when a defect-exhibiting image of the training dataset is applied to the neural network, the tunable parameters being adjusted to simultaneously minimize the loss function for defect-exhibiting images having defect levels throughout the range of defect levels among the two or more defect-exhibiting images of the training dataset.

7. The apparatus according to claim 6, wherein the processing circuitry is further configured to train the neural network using the training dataset that includes another medical image corresponding to the respective defect-minimized image, the another medical image being one of a magnetic resonance image and an X-ray computed tomography image.

8. A method, comprising:

acquiring a reconstructed positron emission tomography (PET) image, the reconstructed PET image reconstructed from emission data representing coincidence counts of respective pairs of gamma rays arising from electron-positron annihilation events, the coincidence counts being detected at a plurality of detector elements;

acquiring a neural network including weighting coefficients of connections between neuronal nodes of respective layers of a plurality of layers between an input layer and an output layer of the neural network, the neural network having been trained using a training dataset that, for a given defect-minimized reconstructed data, includes two or more defect-exhibiting reconstructed data having greater levels of defect than in the defect-minimized reconstructed data, the two or more defect-exhibiting reconstructed data being reconstructed using respective subsets of different sizes of a full PET dataset used to reconstruct the given defect-minimized reconstructed data, the training of the neural network including optimizing a loss function representing respective differences between the given defect-minimized reconstructed data and each of the two or more defect-exhibiting reconstructed data, and applying the reconstructed image to the acquired neural network to generate a defect reduced image.

9. A non-transitory computer readable storage medium including executable instructions, wherein the instructions, when executed by circuitry, cause the circuitry to perform the method according to claim 8.

10. The method according to claim 8, wherein the method further includes:

training the neural network in advance of the emission data being detected at the plurality of detector elements by obtaining the training dataset for training a neural network, the training dataset including a plurality of defect-minimized PET images respectively paired with two or more corresponding defect-exhibiting PET images having various defect levels that are greater than a defect level of the corresponding defect-minimized PET image, wherein, each of the plurality of defect-minimized PET images is reconstructed using a respective full PET emission dataset, and the two or more corresponding defect-exhibiting PET images are reconstructed from different sized subsets of the respective full PET emission dataset that are selected to provide a range of defect levels among the two or more corresponding defect-exhibiting images, and training the neural network by iteratively adjusting tunable parameters of the neural network to minimize a loss function representing a difference between a respective defect-minimized PET image and an output when a defect-exhibiting PET image of the training dataset is applied to the neural network, the tunable parameters being adjusted to simultaneously minimize the loss function for defect-exhibiting PET images having defect levels throughout the range of defect levels among the two or more defect-exhibiting PET images of the training dataset.

11. The method according to claim 10, wherein the method further includes:

training the neural network using the training dataset that includes another medical image corresponding to the respective defect-minimized PET image, the another medical image being one of a magnetic resonance image and an X-ray computed tomography image.

* * * * *